United States Patent [19]
Nishigaki et al.

[11] Patent Number: 5,112,330
[45] Date of Patent: May 12, 1992

[54] RESECTOSCOPE APPARATUS

[75] Inventors: Shinichi Nishigaki, Tokyo; Shiro Bito, Hachioji, both of Japan

[73] Assignee: Olympus Optical Co., Ltd., Tokyo, Japan

[21] Appl. No.: 355,740

[22] Filed: May 23, 1989

[30] Foreign Application Priority Data

| Sep. 16, 1988 | [JP] | Japan | 63-231867 |
| Sep. 17, 1988 | [JP] | Japan | 63-233321 |
| Nov. 2, 1988 | [JP] | Japan | 63-277915 |
| Feb. 28, 1989 | [JP] | Japan | 1-49040 |

[51] Int. Cl.⁵ .................................... A61B 17/36
[52] U.S. Cl. ............................. 606/46; 128/4
[58] Field of Search ............... 606/39, 40, 45–47; 128/4, 6, 7

[56] References Cited

U.S. PATENT DOCUMENTS

| 2,090,923 | 8/1937 | Wappler |
| 3,856,015 | 12/1974 | Iglesias |
| 3,973,568 | 8/1976 | Iglesias |
| 4,134,406 | 1/1979 | Iglesias |
| 4,149,538 | 4/1979 | Mrava et al. ............. 606/46 |
| 4,726,370 | 2/1988 | Karasawa et al. ......... 606/46 X |
| 4,538,610 | 9/1985 | Kubota ................... 606/46 |
| 4,648,399 | 3/1987 | Nakada ................... 606/46 |
| 4,744,361 | 5/1988 | Karasawa ................ 606/46 |

FOREIGN PATENT DOCUMENTS

| 2419131 | of 0000 | Fed. Rep. of Germany |
| 54-33394 | 3/1979 | Japan |
| 57-190542 | 11/1982 | Japan |
| 60-104111 | 7/1985 | Japan |
| 60-149616 | 10/1985 | Japan |
| 61-180001 | 11/1986 | Japan |

Primary Examiner—Robert A. Hafer
Assistant Examiner—Kerry Owens
Attorney, Agent, or Firm—Armstrong, Nikaido, Marmelstein, Kubovcik & Murray

[57] ABSTRACT

The resectoscope apparatus of this invention comprises an elongate hollow sheath to be inserted into a body cavity, an endoscope having an optical system inserted through said sheath and making the body cavity interior observable, an operating part connected to the sheath and a slider made integral with at least one of an electrode inserted through the sheath and making such treatment as resecting or coagulating tissues within a body cavity by using a high frequency current and a cord for feeding the high frequency current from a high frequency current source to the electrode and a slider which is provided in the operating part and can operate the electrode from outside the body.

44 Claims, 40 Drawing Sheets

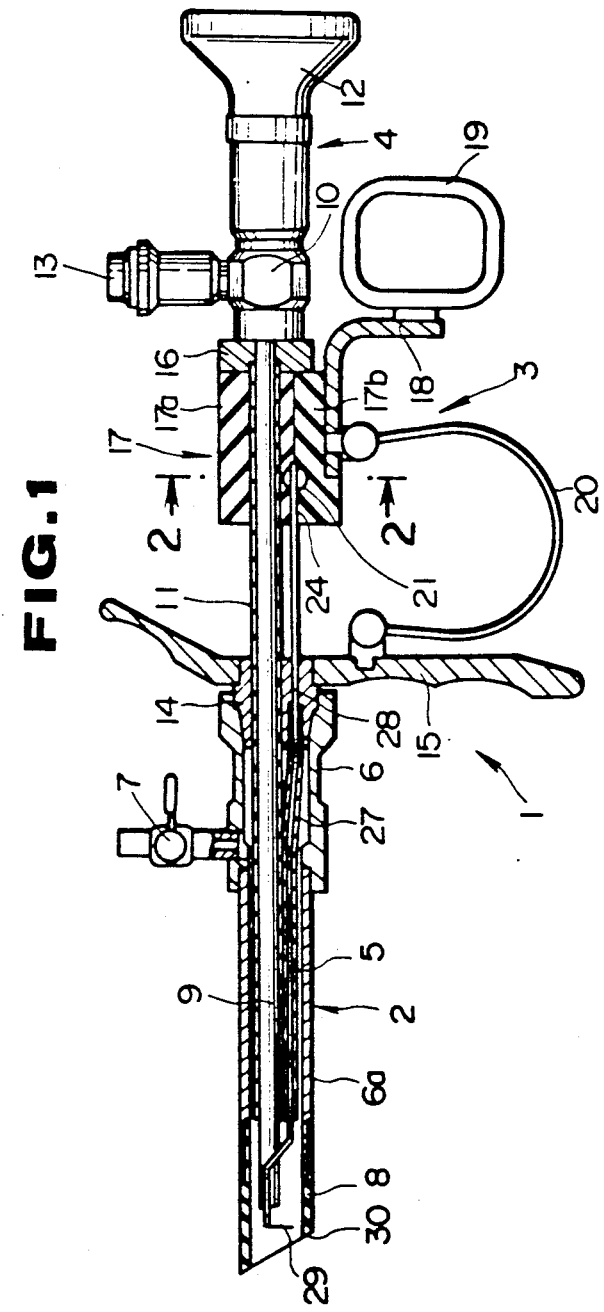

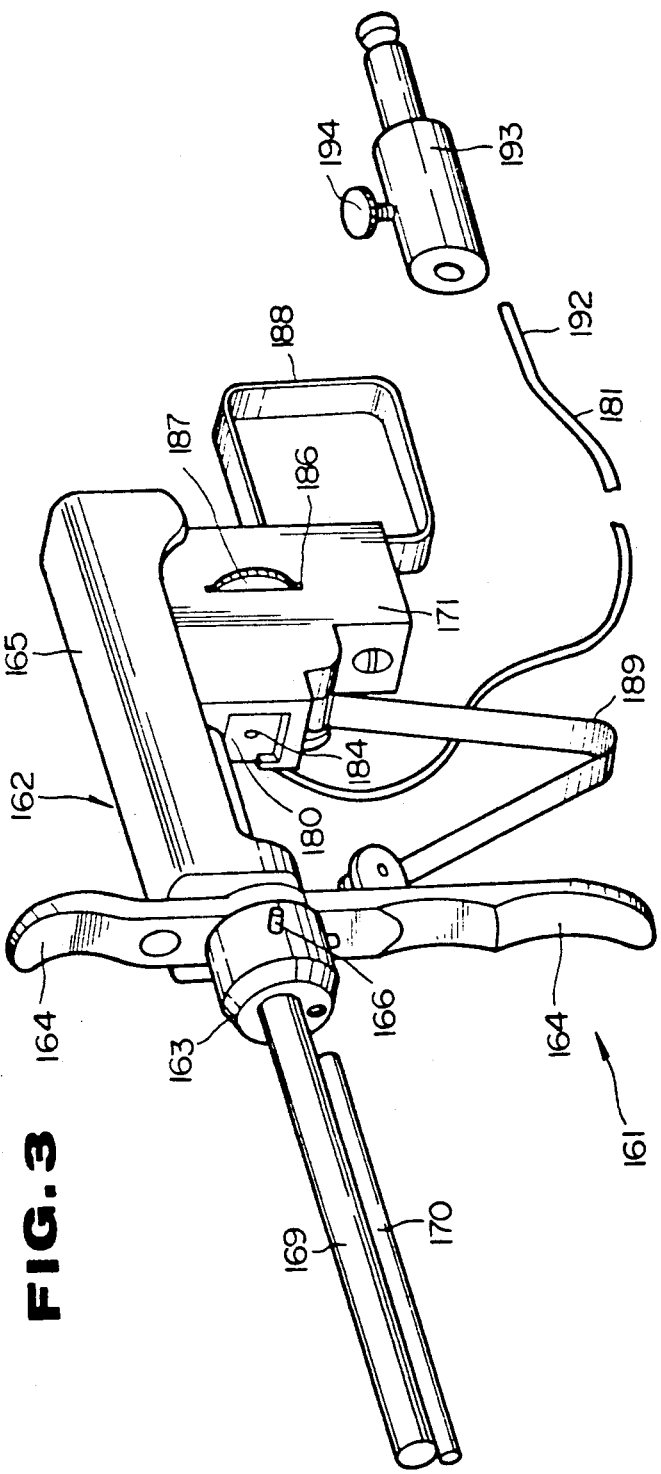
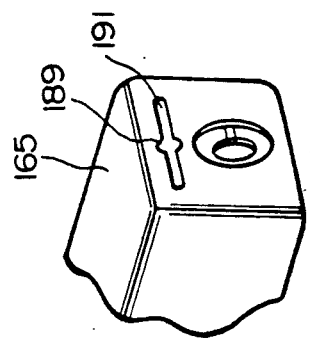
FIG. 3
FIG. 4

FIG.5
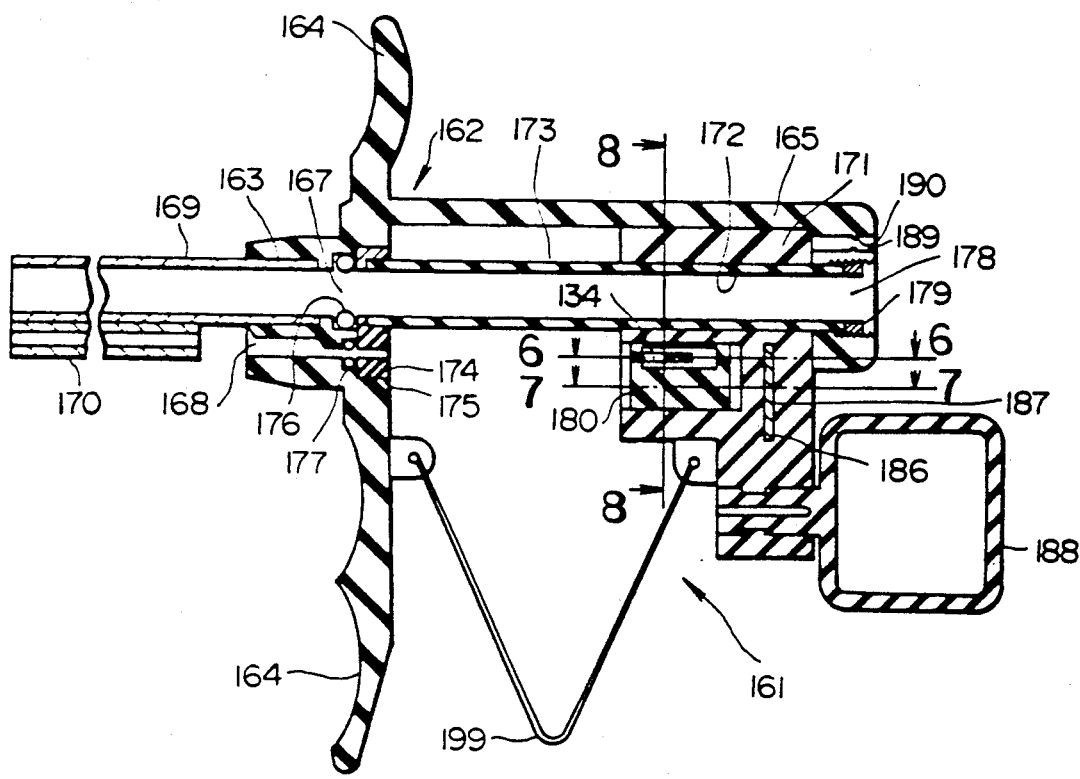
FIG.6 FIG.7 FIG.8
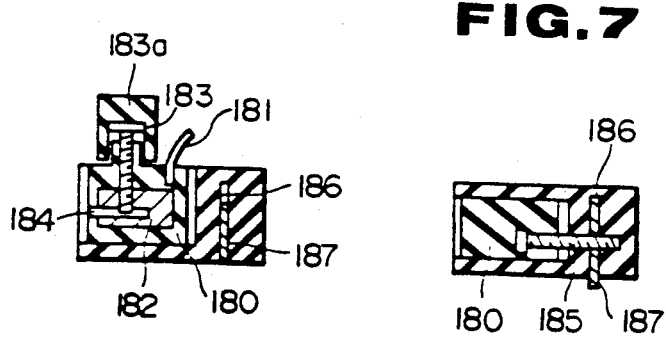

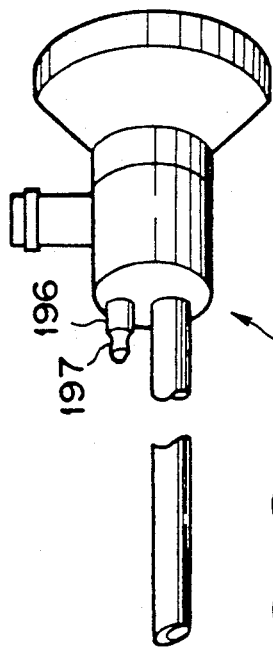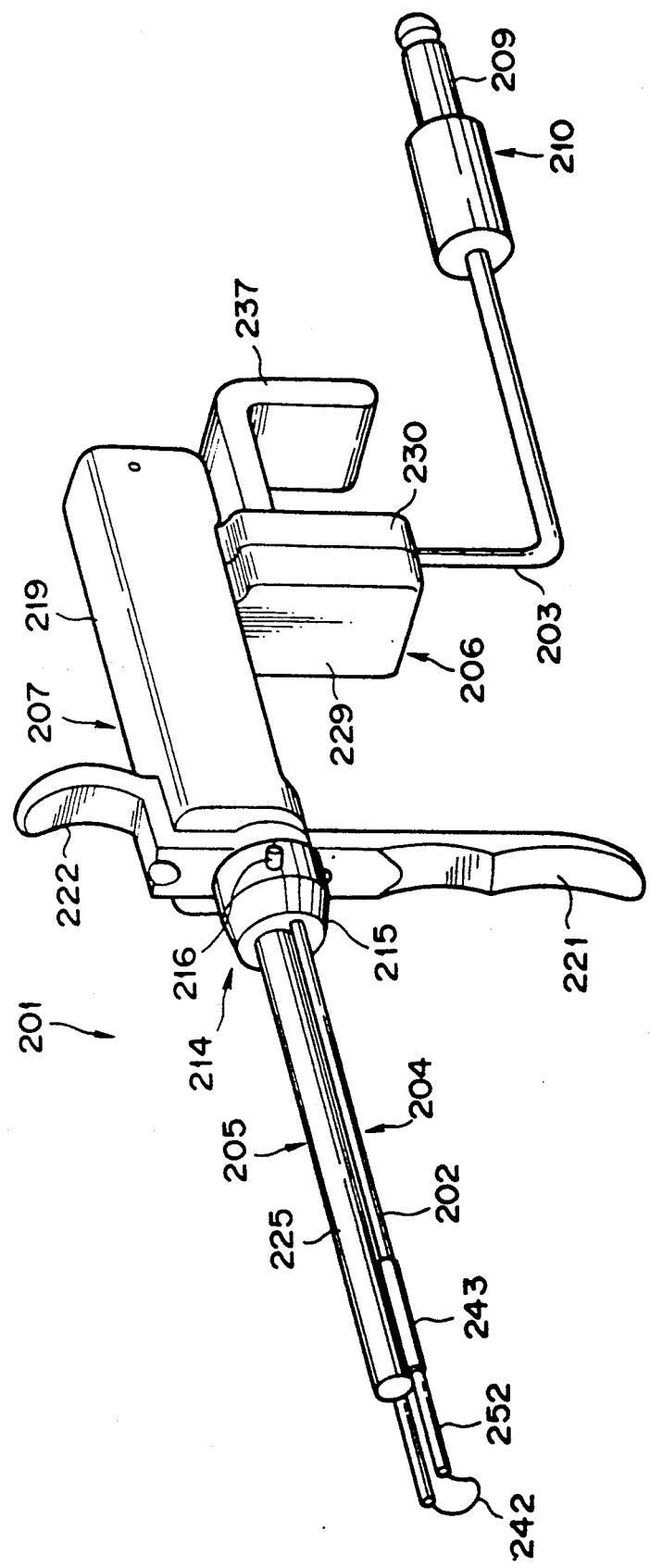

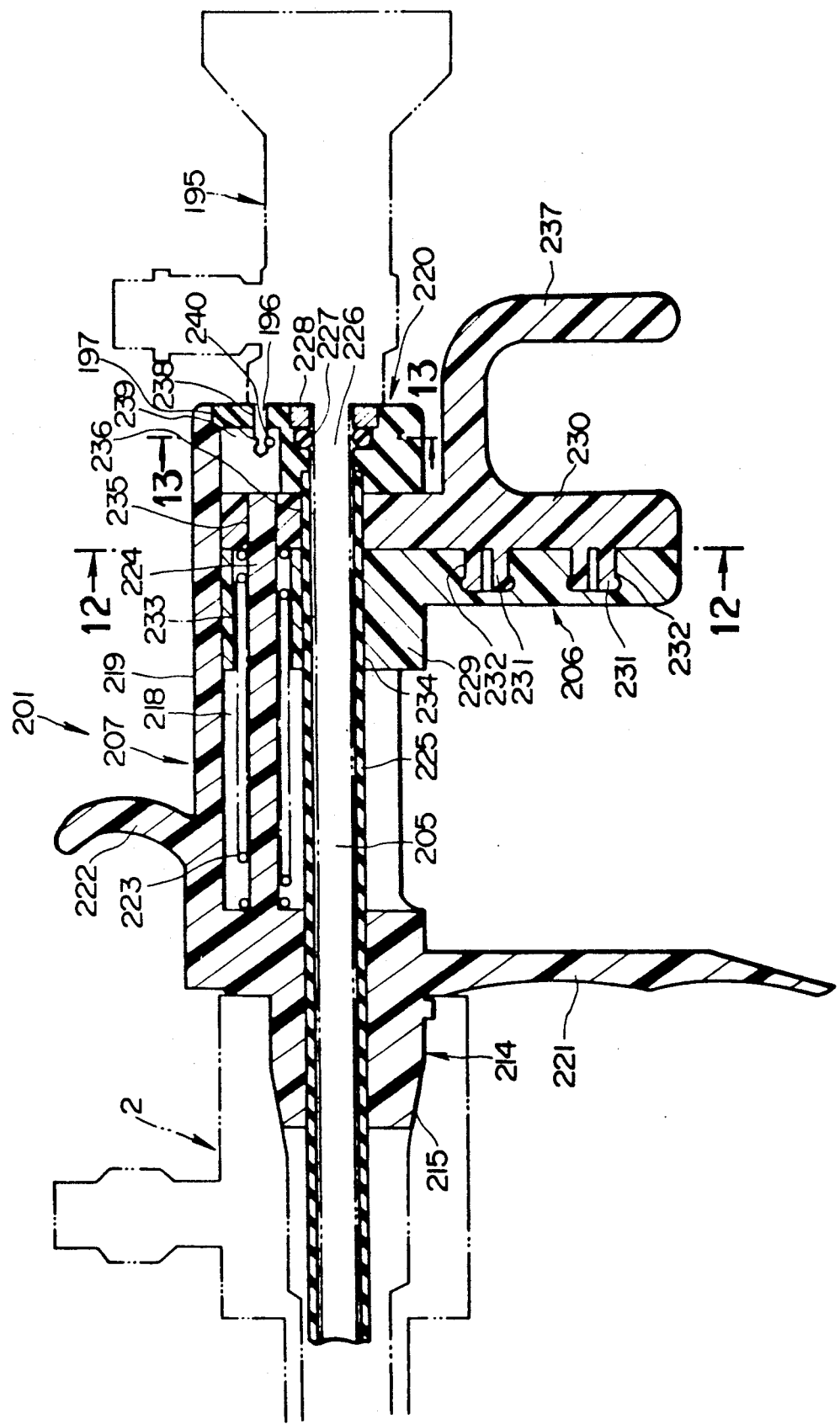

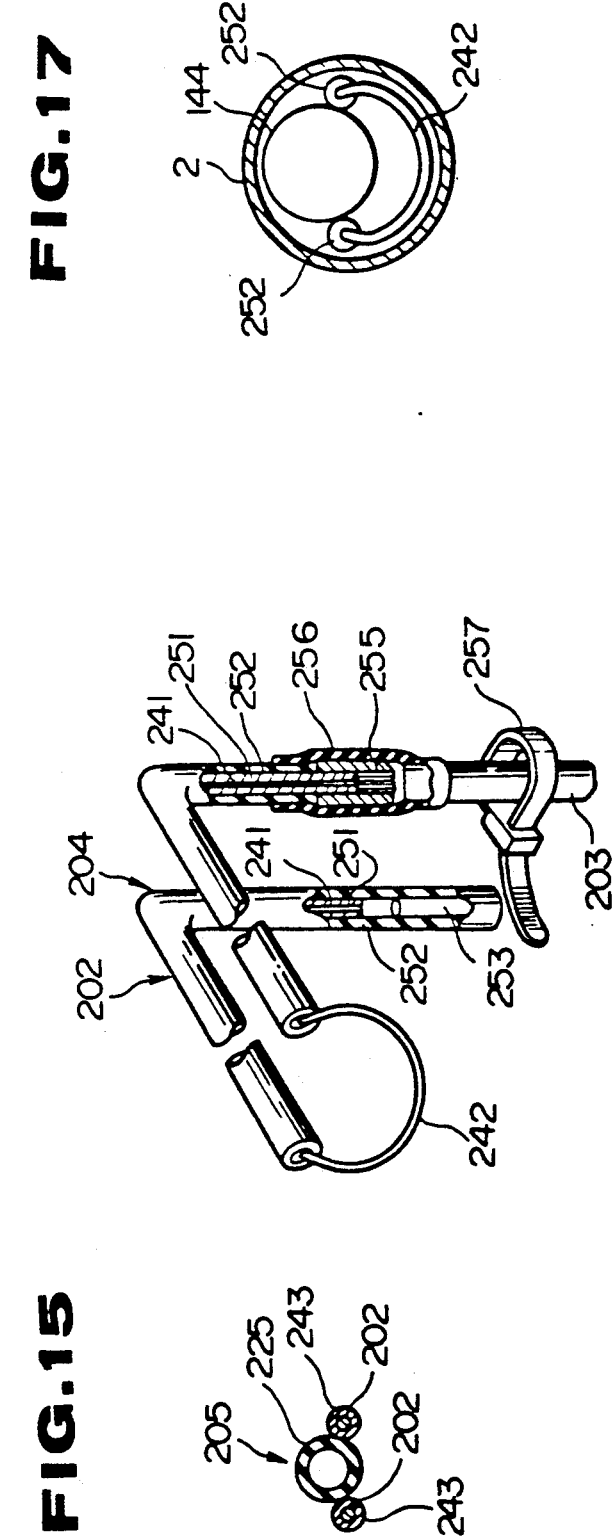

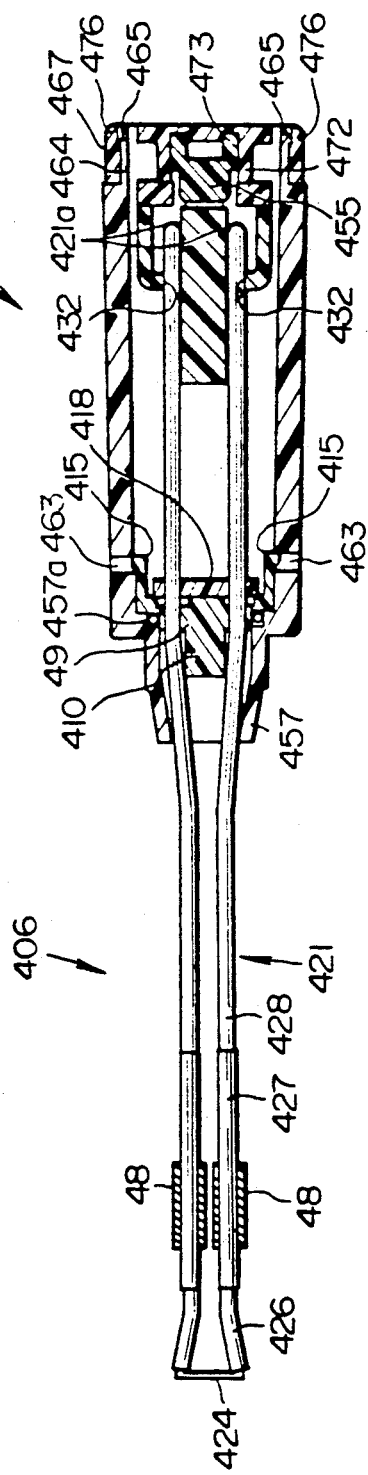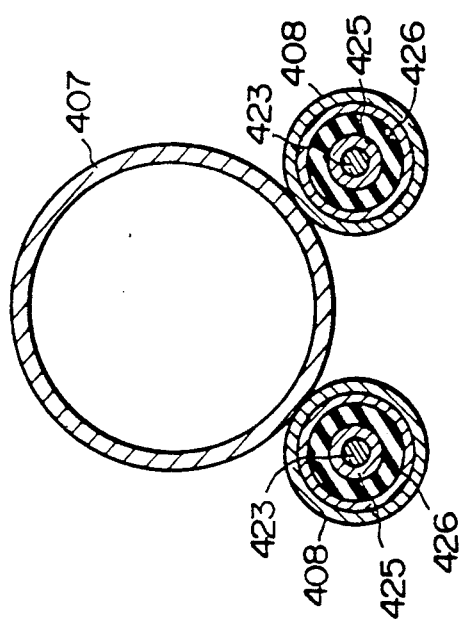

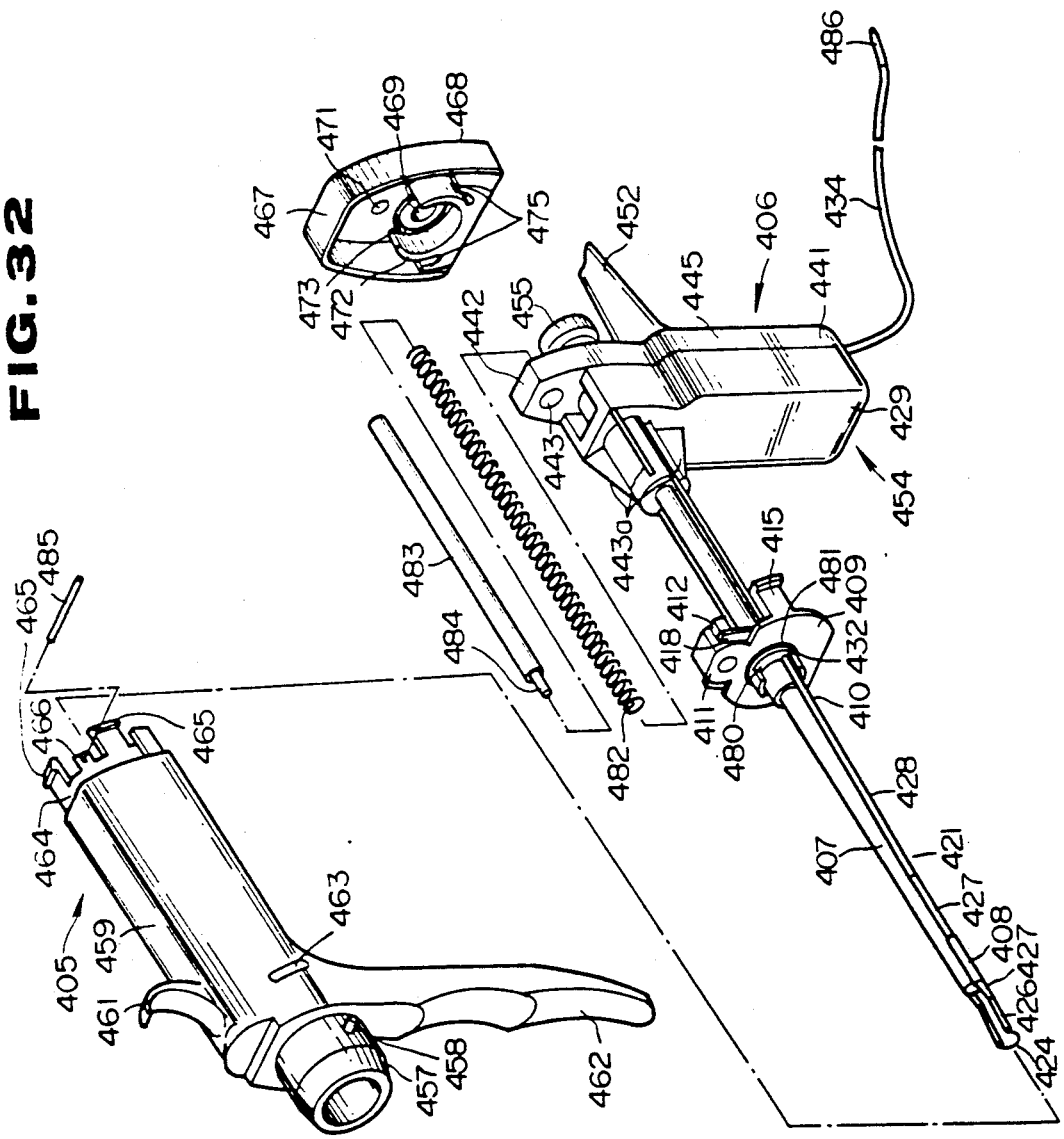

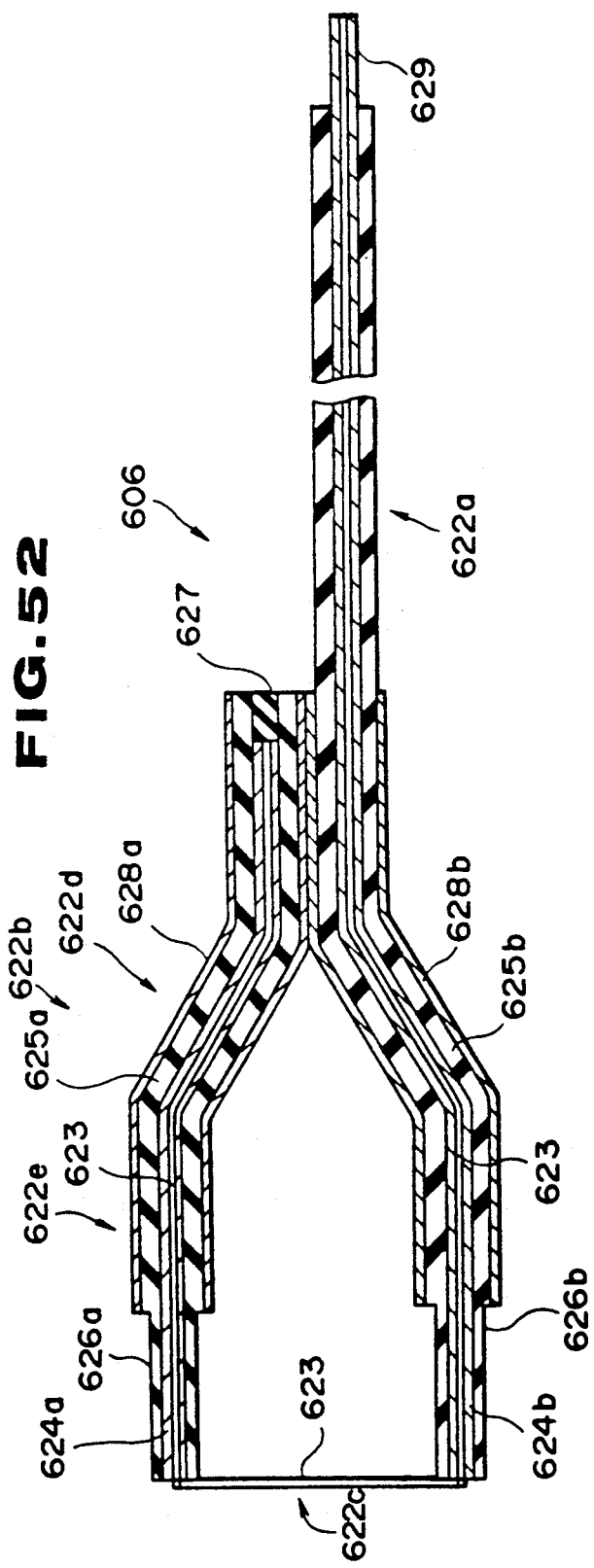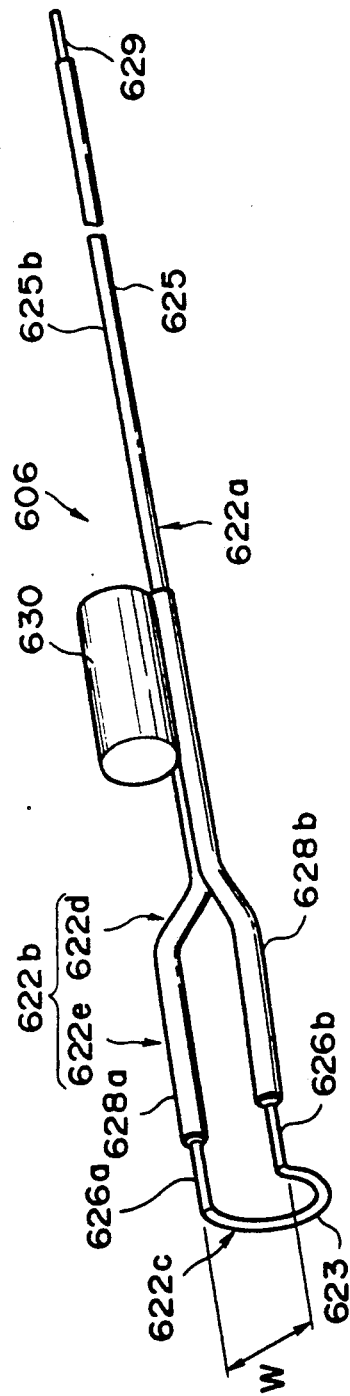

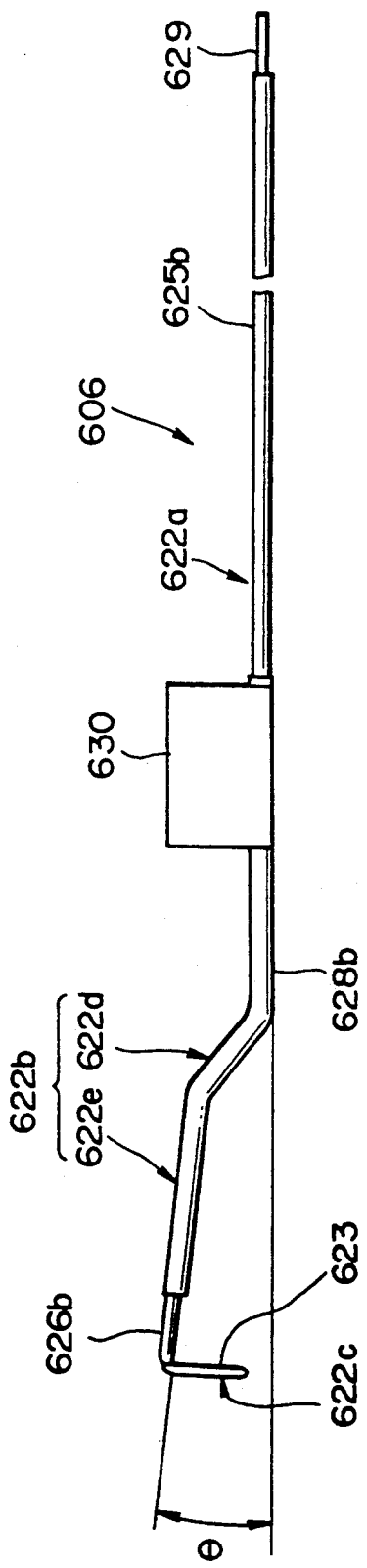

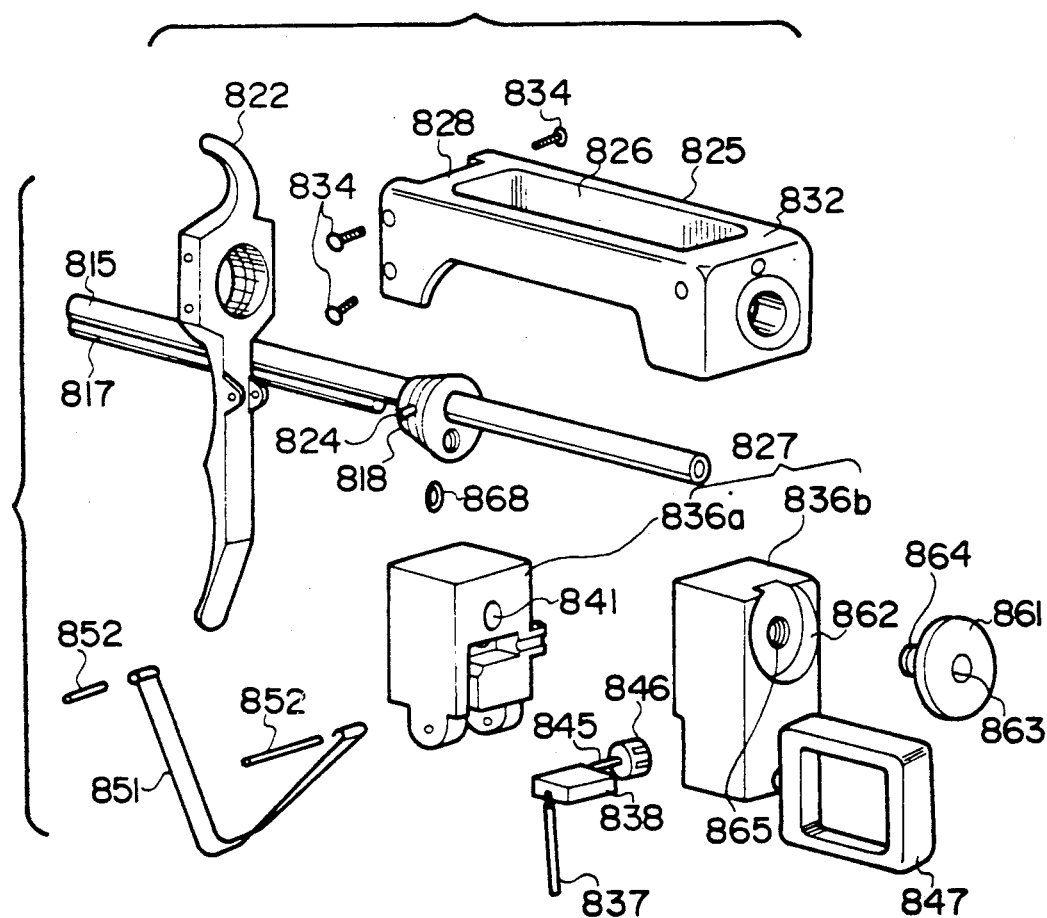

RESECTOSCOPE APPARATUS

FIELD AND BACKGROUND OF THE INVENTION

This invention relates to a resectoscope apparatus for such treatments as resecting and coagulating tissues within a body cavity by using a high frequency current.

Recently, there is extensively utilized an endoscope apparatus whereby internal organs within a body cavity can be observed by inserting an elongate insertable part into the body cavity or various therapeutic treatments can be made, as required, by using treating instruments inserted through a treating instrument channel.

As the above mentioned endoscope apparatus, there is a high frequency endoscope apparatus for resecting a prostate, uterus interior, ureter interior or renal pelvis interior. As such high frequency endoscope apparatus, there is a resectoscope apparatus whereby such treatment as the resection of a prostate can be made by inserting the insertable part into the bladder through the urethra and passing a high frequency electric current through a resecting electrode as shown, for example, in the publication of a Japanese Utility Model Application No. 149616/1985.

Generally, a resectoscope apparatus comprises a hollow sheath to be inserted into a body cavity, an operating part having a slider removably fitted to the rear end side of this sheath and an observing scope (optical sighting tube) removably fitted from the rear end of the operating part to project out of and retract into the rear end of this operating part an electrode made like a loop as branched into two branches at the tip for the resection of tissues within a body cavity.

The above mentioned electrode is removably fitted to the operating part, an electric and mechanical fixing mechanism is provided within the above mentioned slider and a cord for conducting a high frequency current from a current source apparatus to the fixing mechanism is removably fitted to a connector provided in the slider.

However, in case there is an electrode and cord removably fitting mechanism in the slider, it will be difficult to secure the watertightness of the connecting part of the slider with the electrode and of the connecting part of the slider with the cord, and the electric current will be likely to leak through a liquid having come in and to cause a burn or the like. Particularly, in case a disinfecting liquid containing a surface active agent is used, this liquid will have an increased possibility of entering the connecting part, forming an electric path and leaking the electric current.

Also, blood or other fluid will be likely to enter the respective electric connecting parts and the electric conduction and resecting capacity will be reduced by the fluid.

OBJECT AND SUMMARY OF THE INVENTION

An object of the present invention, is to provide a resectoscope apparatus wherein the possibility of electric leak and contact failure are reduced and the electric safety and stability are increased.

A resectoscope apparatus of the present invention comprises an elongate hollow sheath to be inserted into a body cavity, an electrode inserted through the above mentioned sheath for making such treatments as resecting and coagulating tissues within the body cavity by using a high frequency electric current, an operating part for making the above mentioned electrode operatable from outside the body, a cord for feeding a high frequency current from a high frequency current source to the above mentioned electrode and an optical sighting tube having an optical system inserted through the above mentioned sheath for making the body cavity interior observable and wherein at least one of the above mentioned electrode and cord and the above mentioned operating part are made integral.

In the present invention, at least one of the electrode and cord and the operating part are integral and the number of electric contacts between the electrode and cord at which electric leak and contact failure are likely to occur in the operating part is smaller than in the case that the electrode and cord are removably fitted to the operating part.

BRIEF DESCRIPTION OF THE DRAWINGS

FIGS. 1 and 2 relate to the first embodiment of the present invention.

FIG. 1 is a sectioned view of a resectoscope apparatus.

FIG. 2 is a sectioned view on line 2—2 in FIG. 1.

FIGS. 3 to 9 relate to the second embodiment of the present invention.

FIG. 3 is a perspective view showing an operating part of a resectoscope.

FIG. 4 is a perspective view showing the rear part of an operating part body.

FIG. 5 is a sectioned view of an operating part.

FIG. 6 is a sectioned view on line 6—6 in FIG. 5.

FIG. 7 is a sectioned view on line 7—7 in FIG. 5.

FIG. 8 is a sectioned view on line 8—8 in FIG. 5.

FIG. 9 is a perspective view of an optical sighting tube.

FIGS. 10 to 17 relate to the third embodiment of the present invention.

FIG. 10 is a perspective view of a resectoscope apparatus operating part.

FIG. 11 is a vertically sectioned view of an operating part.

FIG. 12 is a sectioned view on line 12—12 in FIG. 11.

FIG. 13 is a sectioned view on line 13—13 in FIG. 11.

FIG. 14 is a partly sectioned side view of an operating part showing an electrode part.

FIG. 15 is a sectioned view on line 15—15 in FIG. 14.

FIG. 16 is a partly sectioned perspective view of an electrode part.

FIG. 17 is an elevation showing position relations of an electrode tip loop, sheath and optical sighting tube as the sheath and optical sighting tube are combined.

FIG. 18 is a perspective view of an operating part.

FIG. 19 is a vertically sectioned view of an operating part.

FIG. 20 is a partly sectioned side view of a resecting handle to show the structure of an electrode part.

FIG. 21 is a sectioned view on line 21—21 in FIG. 20.

FIG. 22 is a sectioned view on line 22—22 in FIG. 20.

FIG. 23 is a perspective view of an electrode part.

FIGS. 24 to 37 relate to the fifth embodiment of the present invention.

FIG. 24 is an appearance view of a resectoscope apparatus operating part.

FIG. 25 is a partly cross-sectioned view of a sheath, operating part and optical sighting tube as combined.

FIG. 26 is a sectioned view in the direction 26—26 in FIG. 25.

FIG. 27 is a sectioned view in the direction 27—27 in FIG. 25 (the sheath and optical sighting tube are omitted).

In FIG. 28, the left side is a sectioned view in the direction 28—28 in FIG. 25 and the right side is an appearance view of the rear surface of an operating part of a resectoscope.

FIG. 29 is a sectioned view in the direction 29—29 in FIG. 28.

FIG. 30 is a sectioned view in the direction 30—30 in FIG. 25.

FIG. 31 is a sectioned view in the direction 31—31 in FIG. 30.

FIG. 32 is a unit disassembled view of an operating part of a resectoscope apparatus.

FIG. 34 is a disassembled view of a connecting part body.

FIG. 35 is a disassembled view of an electrode.

FIG. 36 is a perspective view of a slider front part.

FIG. 37 is a perspective view of a slider rear part.

FIG. 38 is a partly cross-sectioned view of a resectoscope apparatus.

FIG. 39 is a sectioned view in the direction 39—39 in FIG. 38.

FIG. 40 is an appearance view of an electrode.

FIG. 41 is a partly sectioned view of an electrode as seen from below.

FIG. 42 is an explanatory view of an electrode incorporated in an operating part.

FIG. 43 is a partly sectioned view of an operating part.

FIG. 44 is a perspective view of a slider.

FIG. 45 is an explanatory view of the rear end part of an electrode.

FIG. 46 is an explanatory view of a C-ring.

FIG. 47 is an explanatory view of an A-cord.

FIG. 48 is a partly sectioned view of an operating part.

FIG. 49 is a perspective view of a front slider.

FIG. 50 is a perspective view of a rear slider.

FIG. 51 is a sectioned view in the direction 51—51 in FIG. 48.

FIGS. 52 to 55 relate to the tenth embodiment of the present invention.

FIG. 52 is a sectioned view of an electrode.

FIG. 53 is a side view of an electrode.

FIG. 54 is a perspective view of an electrode.

FIG. 55 is an explanatory view showing an electrode within a sheath.

FIG. 56 is a sectioned view of an electrode.

FIG. 57 is a perspective view of an electrode.

FIGS. 58 to 63 relate to the 12th embodiment of the present invention.

FIG. 58 is a sectioned view of an operating part.

FIG. 59 is an appearance view of a resectoscope apparatus.

FIG. 60 is a sectioned view on line 60—60 in FIG. 58.

FIG. 61 is a sectioned view on line 61—61 in FIG. 58.

FIG. 63 is a perspective view of an operating part as disassembled into main component parts.

FIG. 62 is a sectioned view showing position relations of an optical sighting tube, electrode and sheath tip part.

DETAILED DESCRIPTION OF PREFERRED EMBODIMENTS OF THE INVENTION

Figure 12:
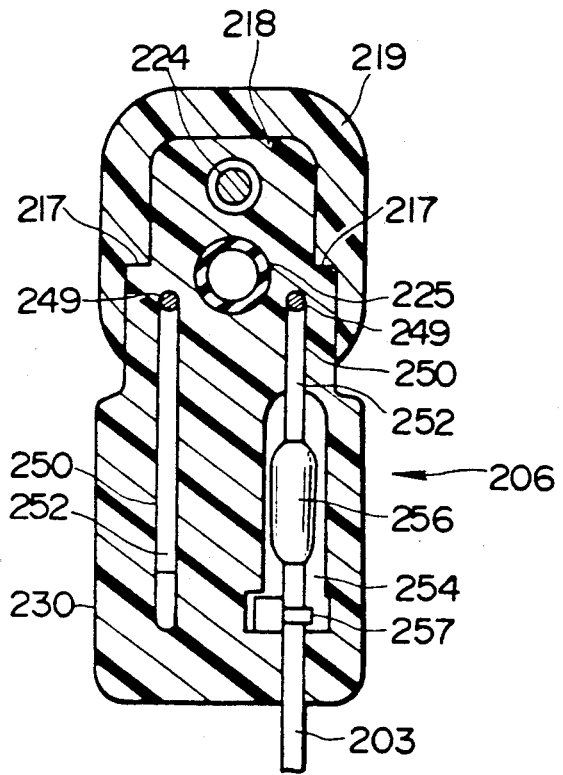
Figure 13:
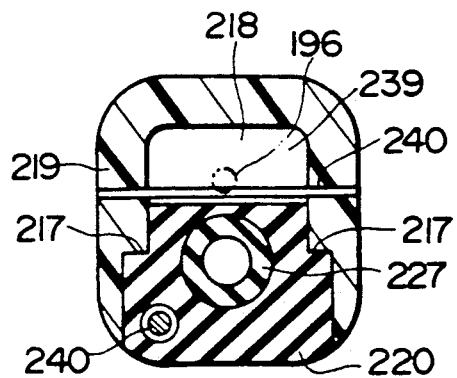

FIGS. 1 and 2 show the first embodiment of the present invention.

As shown in FIG. 1, a resectoscope apparatus 1 is formed of a combination of a sheath 2, an operating part 3 removably fitted to the rear of the above mentioned sheath 2, an optical sighting tube for observation inserted through the above mentioned sheath 2 from the rear of the above mentioned operating part 3 and an electrode 5 inserted through the above mentioned sheath 2 from the above mentioned operating part 3.

The above mentioned sheath 2 comprises an elongate hollow tube part 6a insertable into a body cavity and a sheath body 6 connected to the base end part of this hollow tube part 6a and consisting of a tubular body communicating with the interior of the above mentioned hollow tube part 6a. The above mentioned sheath body 6 is provided with a water feeding port 7 for injecting a liquid. A beak 8 made of an insulating material is fitted to the tip of the hollow tube part 6.

The above mentioned optical sighting tube 4 comprises an insertable part 9 inserted through the above mentioned sheath 2 and a hand base part 10 connected to the rear end of this insertable part 9. A light guide and observing optical system not illustrated are provided within the above mentioned insertable part 9. An eyepiece 12 and a light guide connecting part 13 to be connected with a light guide cable not illustrated are provided on the above mentioned hand base part 10. The light from the light guide cable not illustrated is emitted from the tip of the insertable part 9 by the light guide within the insertable part 9 through the above mentioned light guide connecting part 13 to illuminate an affected part. The image of the affected part is transmitted to the hand base part 10 by the observing optical system within the insertable part 9 so as to be observable by the operator through an opening at the rear end of the eyepiece 12.

The above mentioned operating part 3 is provided with a guide tube 11 for leading the above mentioned optical sighting tube 4 through the sheath 2. A sheath connecting part 14 for removably connecting and fixing the sheath 2 to the sheath body 6 is fitted and fixed to the outer periphery of the midway part of this guide tube 11. This sheath connecting part 14 removably fits and fixes the sheath 2 to the sheath body 6 so as to fix the above mentioned guide tube 11 to the sheath 2 in a fixed position. Further, a finger hanger 15 projecting in the vertical direction is fitted to the above mentioned sheath connecting part 14.

On the other hand, a fixing part 16 for positioning and fixing the optical sighting tube 4 in a fixed position is fitted and fixed to the rear end of the above mentioned guide tube 11. As positioned between this fixing part 16 and the above mentioned sheath connecting part 14, a slider 17 for operating the electrode is fitted slidably forward and rearward on the outer periphery of the above mentioned guide tube 11. That is to say, this slider 17 is movable between the sheath connecting part 14 and fixing part 16. A thumb hanging ring 19 is fitted through an L-shaped plate 18 in the lower rear of the above mentioned slider 17. A plate spring 20 is hung between the above mentioned slider 17 and finger hanger 15 so that the slider 17 may stand by as butted against the fixing part 16 by the returning force of this plate spring 20.

In this embodiment, the above mentioned slider 17 has a slider upper part 17a and slider lower part 17b between which an electrode receptacle 21 formed of a conductive material is inserted and is made integral by such means as bonding. As shown in FIG. 2, an electrode cord 23 provided at one end with a current source plug 22 connected to a high frequency current source apparatus not illustrated is secured as kept watertight from outside the slider 17 to the above mentioned electrode receptacle 21. Also, as shown in FIG. 1, the above mentioned slider 17 and electrode receptacle 21 are provided in the direction parallel with the guide tube 11 with an electrode inserting hole 24 so that the electrode 5 may be inserted. Further, a set screw 25 is screwed in the lengthwise direction into the electrode receptacle 21 so as to be free to project and retreat at the tip out of and into the electrode inserting hole 24. Also, a grip 26 made of an insulating material is fitted to the rear end of this set screw 25.

Below the guide tube 11 on the tip side from the above mentioned sheath connecting part 14, an electrode inserting hole 27 is provided and is led at the rear end to an electrode inserting hole 28 provided in the sheath connecting part 14.

The above mentioned electrode 5 is inserted into the electrode inserting tube 27 from the tip, is led at the rear end to the electrode inserting hole 24 provided in the slider 17 and electrode receptacle 21 through the sheath connecting part 14 and is fixed to the electrode receptacle 21 by the set screw 25 so that the current source plug 22 may be electrically connected to the loop 29 at the tip of the electrode 5.

The operation of this embodiment shall be explained in the following.

First of all, the electrode 5 is fixed to the electrode receptacle 24 within the slider 17 and the current source plug 22 is connected to a high frequency current source apparatus not illustrated. Next, the hollow tube part 6a of the sheath 2 is inserted into a body cavity, the thumb of one hand is hung on the thumb hanging ring 19, the remaining fingers are hung on the finger hanger 15 and the slider 17 is advanced. Then, the electrode 5 will also advance and the loop 29 will be able to be projected out of the tip of the sheath 2. Then, while being observed with the optical sighting tube 4, when an affected part is positioned between the tip 30 of the sheath 2 and the loop 29 and the pushing of the slider 17 is released, the slider will be retreated by the energizing force of the plate spring 20, the above mentioned loop 29 will also retreat with it and therefore the above mentioned affected part will be able to be inserted between the tip 30 and loop 29. At this time, if a high frequency current is fed from the current source apparatus, the affected part will be able to be burnt off.

As described above, in the conventional resectoscope, generally, as the electrode and electrode cord are removably fitted to the slider of the insertable part, a current leak and contact failure in the connecting part will be likely to occur.

On the other hand, according to this embodiment, as the electrode cord 23 is made integral with the slider 17 and is sealed as insulated from outside, the electric current will be able to be prevented from leaking from between this electrode cord 23 and slider 17. Also, as the electric contact is only in the removably fitting part between the electrode 5 and slider 17, the probability of the contact failure will be able to be reduced. From these facts, it is possible to elevate the electric safety and stability.

FIGS. 3 to 9 show the second embodiment of the present invention.

In this embodiment, a body 162 of an operating part 161 is formed of a sheath connecting part 163, finger hanger 164 and case part 165 provided in the rear of these which are integrally molded of such insulating material as plastics.

The insulating material is, for example, polycarbonate (abbreviated as PC), polyacetal (polyoxymethylene)(abbreviated as POM), polyphenylene oxide (abbreviated as FPO), polysulfone (abbreviated as PSU), polyphenylene sulfide (abbreviated as PPS) or polyether imide (abbreviated as PEI) or may be also such ceramics as glass ceramics made by depositing mica (fluorine gold mica).

As shown in FIG. 3, the above mentioned sheath connecting part 163 is provided symmetrically on the right and left with connecting pins 166 for connecting a sheath not illustrated. Also, as shown in FIG. 5, an optical sighting tube inserting hole 167 and electrode inserting hole 168 are formed within the sheath connecting part 163. A guide tube 169 for inserting an optical sighting tube 195 shown in FIG. 9 is fitted in the above mentioned optical sighting tube inserting hole 167. An electrode inserting tube 170 is secured to the lower part of this guide tube 169.

As shown in FIG. 5, a slider 171 is fitted slidably forward and rearward in the above mentioned case part 165. An insulating pipe inserting hole 172 is formed in the sliding direction in the above mentioned slider 171. An insulating pipe 173 made of such insulating material as plastics is inserted through this insulating pipe inserting hole 172, is fitted at one end into an O-ring presser 174 which is fitted into an O-ring presser fitting part 175 of the body 162 and fixes O-rings 176 and 177 fitted respectively to the optical sighting tube inserting hole 167 and electrode inserting hole 168, is inserted at the other end into an optical sighting tube inserting hole 178 in the rear part of the body 162 and is pressed against the O-ring presser 174 by a nut 179 screwed into this optical sighting tube inserting hole 178. That is to say, the O-ring presser 174 and slider 171 are fixed to the body 162 by the nut 179 through the insulating pipe 173. Therefore, in such structure, if the nut 179 is removed, the insulating pipe 173, O-ring presser 174, O-rings 176 and 177 and slider 171 will be able to be disassembled from the body 162 and to be easily replaced.

Also, as shown in FIGS. 5 to 8, an electrode fixing mechanism 180 is fitted slidably forward and rearward to the above mentioned slider 171, is sealed with such insulating material as plastics on the periphery of an electrode receptacle 182 fitted with an electrode cord 181 and has a set screw 183 screwed in. The above mentioned set screw 183 projects at the tip into an electrode inserting hole 184. A grip 183 made of an insulating material is fixed to the set screw 183 at the other end.

Further, a positioning screw 185 is fixed to the above mentioned electrode fixing mechanism 180 and is screwed into a positioning ring 187 inserted into a positioning ring inserting hole 186 formed in the slider 171. That is to say, the electrode fixing mechanism 180 is fixed to the slider 171 by the positioning screw 185 and positioning ring 187 so that, by rotating the positioning ring 187, the position of the electrode fixing mechanism 180 with respect to the slider may be adjusted.

A finger hanging ring 188 formed of such insulating material as plastics is rotatably fitted by snap fitting in the lower part of the above mentioned slider 171.

A V-shaped plate spring 199 is rotatably fixed at the respective ends to the finger hanger 164 of the body 162 and the slider 171 so that the slider 171 may be energized by this plate spring 199 to stand by as butted against the rear part of the body 162.

As shown in FIG. 5, a connecting pin inserting hole 189 is formed in the rear part of the body 163 and a projection 190 is formed on the inner surface of this connecting pin inserting hole 189. Also, as shown in FIG. 4, a slit 191 is provided in the lateral direction in the above mentioned connecting pin inserting hole 189. In case such optical sighting tube 195 as is shown in FIG. 9 is to be connected to the operating part 161, when the connecting pin 196 is inserted into the connecting pin inserting hole 189, as the insulating material forming the body 162 has a resiliency, the projection 190 will be pushed and expanded in the vertical direction. When the groove 197 of the connecting pin 196 reaches the projection 190, the pushed and expanded projection 190 will tend to return to the original state and will fit in the groove 197 and the optical sighting tube 195 will be connected to the operating part 161.

As shown in FIG. 3, when an electrode cord 181 is inserted in the tip part 192 into a current source connecting plug 193 and a fixing screw 194 is fastened, the current source connecting plug 193 will be able to be fitted.

Thus, according to this embodiment, as the electrode fixing mechanism 180 and current source cord 181 are sealed as electrically connected with each other, the current can be prevented from leaking from this part and no contact failure is likely to occur.

The other formations, operations and effects are the same as in the first embodiment.

FIGS. 10 to 17 show the third embodiment of the present invention.

Figure 14:
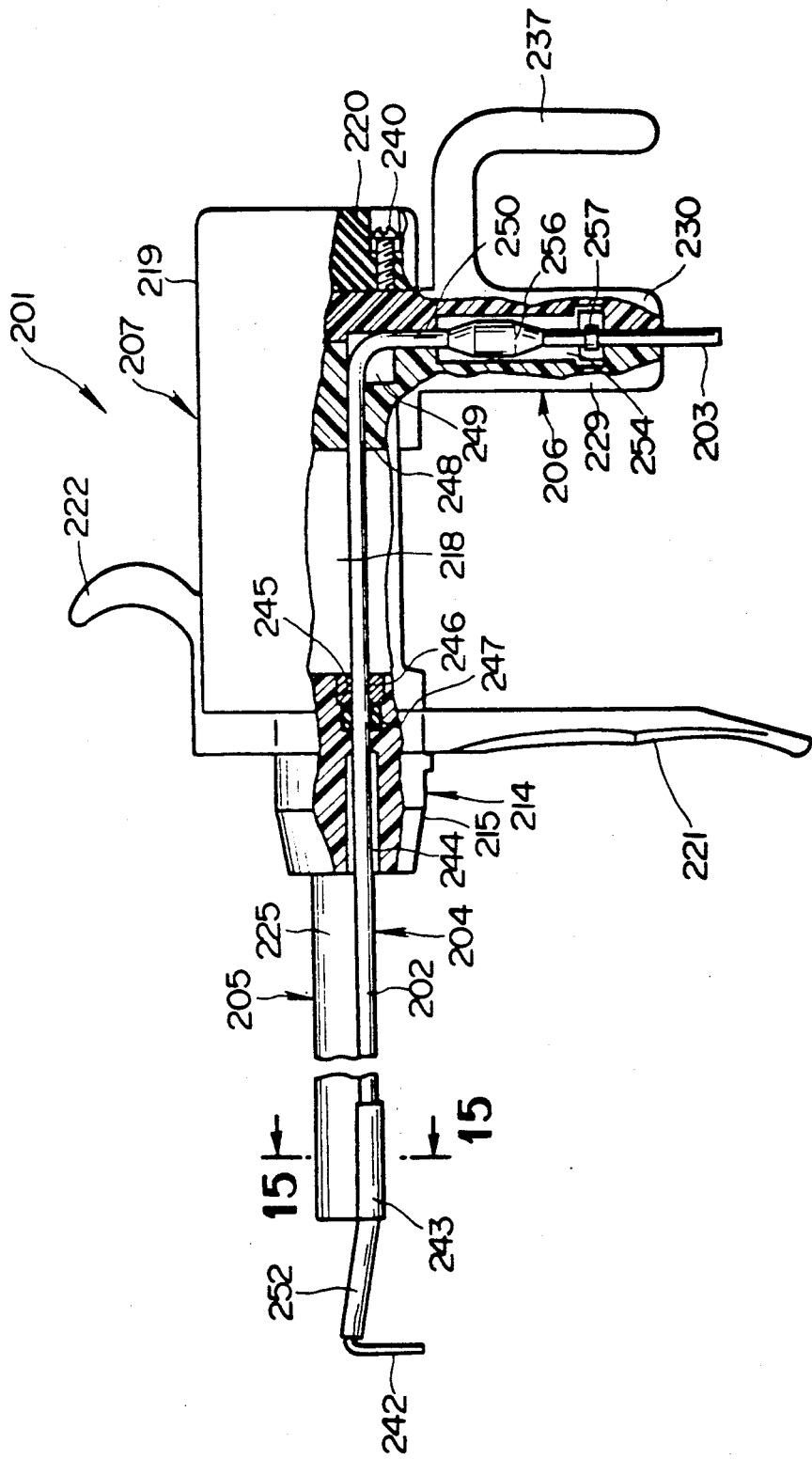
Figure 18:
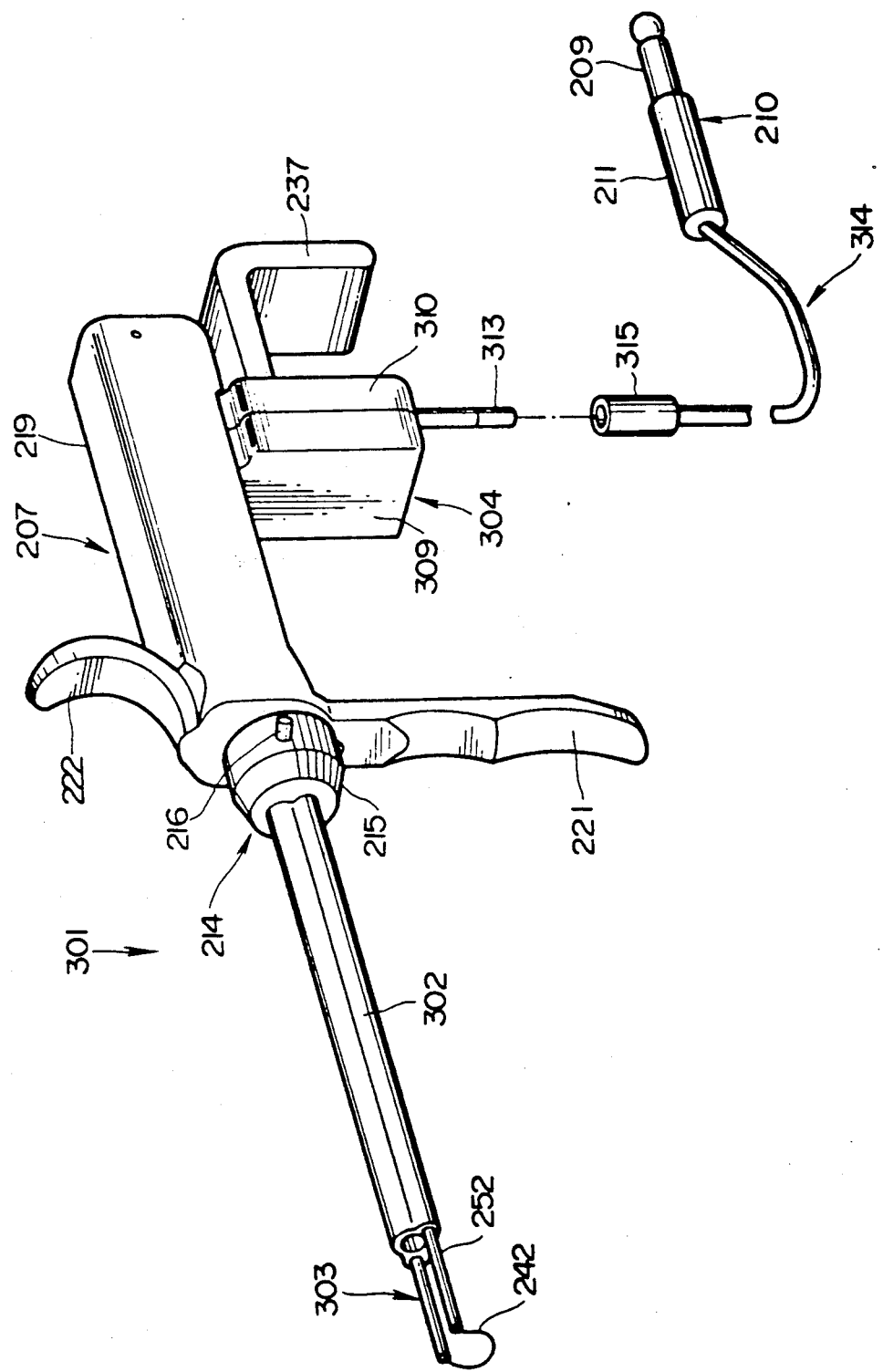
FIGS. 18 to 23 relate to the fourth embodiment of the present invention.
Figure 19:
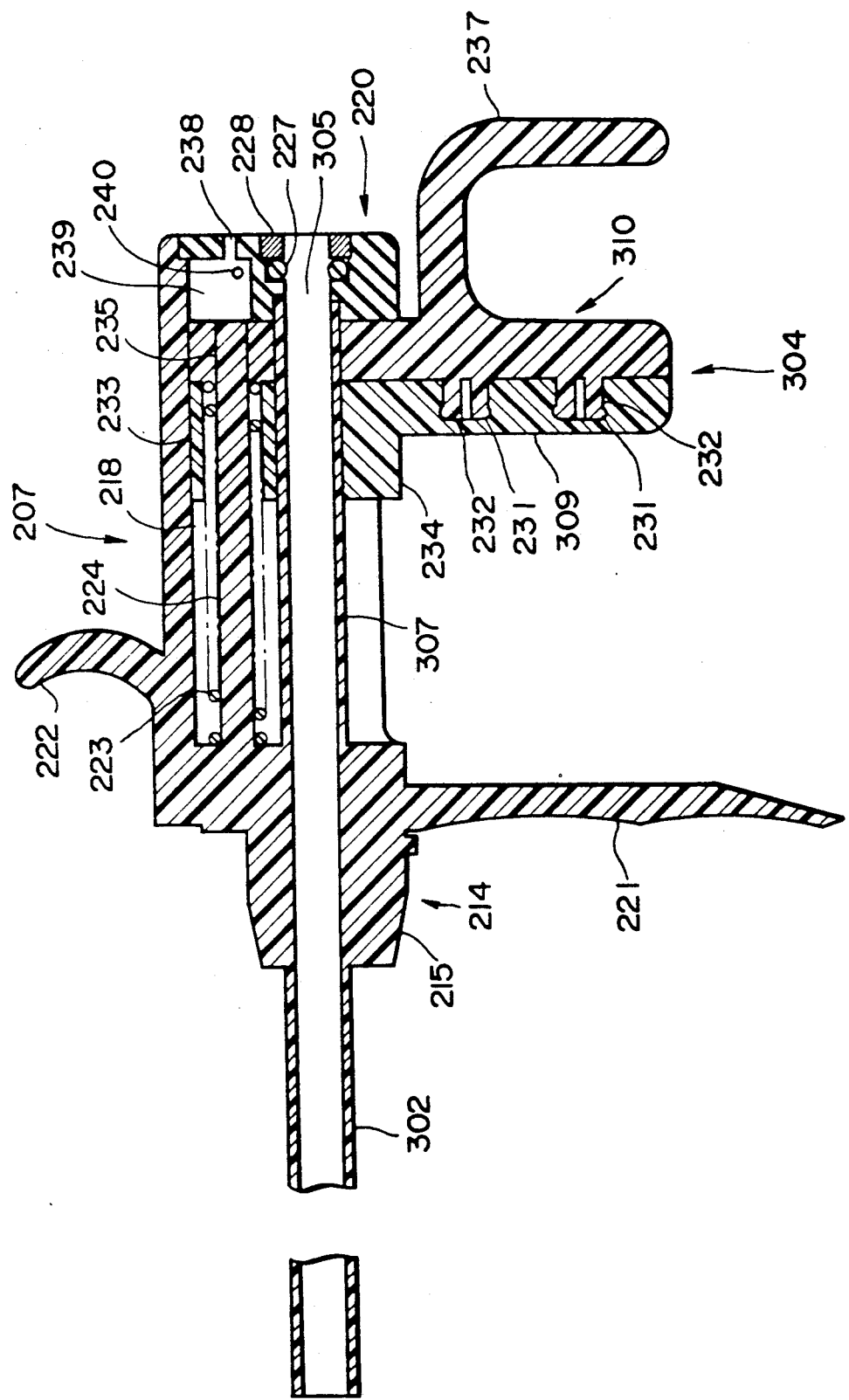

As shown in FIGS. 10, 11 and 14, an operating part 201 comprises an electrode 204 formed integrally with an electrode part 202 and cord part 203, an optical sighting tube inserting part 205 in which such optical sighting tube 195 as is shown in FIG. 9 is inserted and connected, a slider part 206 in which the electrode 204 is slid forward and rearward and a body 207. As shown in FIG. 10, a plug 210 electrically connectable with a high frequency current source not illustrated when an inserting part 209 is inserted is connected to the end of the above mentioned cord part 203 so that the cord part 203 and high frequency current source not illustrated may be electrically and mechanically connected with each other.

The operating part 201 is removably connectable watertightly with such sheath 2 as is shown in FIG. 1 by a tapered part 215 and pins 216 (See FIG. 10) of a connecting part 214 formed in front of the body 207. In the rear of the above mentioned connecting part 214, as shown in FIG. 12, a cover 219 of a substantially square cross-sectional shape having a groove, 218 having a rectangular cross-sectional shape formed with steps 217 and opened below is extended to an optical sighting tube connecting part 220 formed at the rear end of the optical sighting tube connecting part 220. A lower finger hanger 221 on which the middle finger and third finger may be hung in case the operating part 201 is held with one hand is provided to project downward from near the connecting part 214 of the above mentioned cover 219 and an upper finger hanger 222 on which the forefinger may be hung is provided to project, upward.

In the upper portion of slider 206 within the above mentioned groove 218, a spring shaft 224 slidably holding a spring 223 always rearward energizing the slider 206 projects rearward from the front. Connecting part 214, tapered part 215, pin 216, cover 219, lower finger hanger 221, upper finger hanger 222 and spring shaft 224 are formed of plastics and are integrally molded as a unit. Below cover 219 within the groove 218, a guide tube 225 formed of such insulating material as plastics is extended to the optical sighting tube connecting part 220 through the connecting part 215 from the front of the connecting part 215. In the optical sighting tube connecting part 220, an optical sighting tube inserting hole 226 having substantially the same inside diameter as the inside diameter of the guide tube 225, O-ring 227 and O-ring presser 228 fixing this O-ring 227 are adjacently provided in the rear so that the optical sighting tube 195 may be inserted through the guide tube 225 while keeping watertightness and may be led at the tip to the tip part of the operating part 201.

The above mentioned slider part 206 consists of a slider front part 229 and slider rear part 230 formed of such insulating material as plastics and are made integral by engaging a snap fit 231 projecting forward from the slider rear part 230 and a hole 232 formed in the slider front part 229 with each other. The upper contour of the above mentioned slider front part 229 and slider rear part 230 is substantially the same as the shape of the groove 218. In the slider front part 229, there are formed a spring hole 233 through which a spring 223 can be inserted and a guide tube inserting hole 234 through which a guide tube 25 can be inserted. In the slider rear part 230, there are formed a shaft hole 235 through which the spring 223 can not be inserted but only the spring shaft 224 can be inserted and a guide tube inserting hole 236 through which the guide tube 225 can be inserted. The above mentioned slider front part 229 and slider rear part 230 are contained integrally slidably forward and rearward within the groove 218 within the cover 219.

A thumb hanger 237 which will prevent the thumb hung on the slider rear part 230 from slipping in case the operating part 201 is held with one hand is provided in the rear of the lower part of the above mentioned slider rear part 230 so that, when the thumb is pushed out forward, the slider part 206 may be slid forward within the groove 218 against the force of the spring 223 and, when the force of the thumb is released, the slider 206 may be energized by the spring 223 to move to the optical sighting tube connecting part 220.

A pin hole 238 in which the connecting pin 196 of the optical sighting tube 195 (See FIG. 9) can be inserted is provided above the optical sighting tube inserting hole 226 of the above mentioned optical sighting tube connecting part 220 so that, when the groove 197 of the optical sighting tube 195 engages a piano wire 240 hung within a space 239 in front of the pin hole 238, the optical sighting tube 195 may be removably connected to the operating part 201. By the way, a screw 260 is screwed projectably toward the groove 218 from the optical sighting tube connecting part 220 so that the displacement within the groove 218 of the slider part 206 may be regulated. (See FIG. 14).

As shown in FIGS. 16 and 17, at the tip of the electrode part 202 projected forward from the tip of the above mentioned optical sighting tube inserting part 205, a wire 241 as exposed is formed as a loop 242 which can resect tissues within a body when a high frequency current is passed. The above mentioned wire 241 is coated with stainless steel pipes 251 except on the loop 242 and is further insulated and coated thereon with Teflon tubes 252. The above mentioned electrode part 202 is held by being inserted through guide pipes 243 fixed on both sides of the guide tube 225 from both ends of the above mentioned loop 242, is further inserted through inserting holes 244 formed in the connecting part 214 and O-rings 247 fitted by O-ring pressers 246 fitted in O-ring holes 245 contained in O-ring holes 245 communicating with the 248 and spaces 249 provided in the slider front part 229 of the slider part 206. This electrode part 202 is bent downward within the spaces 249 and is led to grooves 250 provided between the slider front part 229 and slider rear part 230.

By the way, at one end of the electrode part 202 led to the groove 250 of the slider part 206, as shown in FIG. 16, the end surfaces of the wire 241 and stainless pipe 251 are positioned within the Teflon tube 252 and the watertightness of the end surface of the Teflon tube 252 is secured by pressing plastics 253 into the Teflon tube 252. At the other end of the electrode part 202, the wire 241 and stainless steel Pipe 251 project from the Teflon tube 252 and the cord part 203 at the end and the stainless steel pipe 251 are pressed and connected with a calking pipe 255 as electrically connected with each other within a space 254 communicating with the lower part of the groove 250 and are further insulated and coated thereon with a thermocontracting tube 256. A clamp 257 is wound on the cord part 203 in the position of the lower end of the above mentioned space 254 so that the clamp 257 will catch on the lower end of the above mentioned space 254 and the cord part 203 will not be removed even if pulled from below.

Thus, in this embodiment, as the electrode and electrode cord are connected with each other within the slider part 206 and the connecting part is made integral with the slider part 206 by being inserted while kept watertight by the slider front part 229 and slider rear part 230 as insulated and coated with the thermocontracting tube 256, a current leak and contact failure will never be likely to occur. That is to say, as the parts other than the electrode tip part and current source cord end are perfectly insulated and coated, there will be no current leak in the intermediate part and, as there is no such movable part as the electrode fixing mechanism in the slider part 206, no contact failure will be likely to be caused by an operation failure and a high electric safety and electric stability will be obtained.

The other formations, operations and effects are the same as in the first embodiment.

FIGS. 18 to 23 show the fourth embodiment of the present invention.

Figures 20, 21:
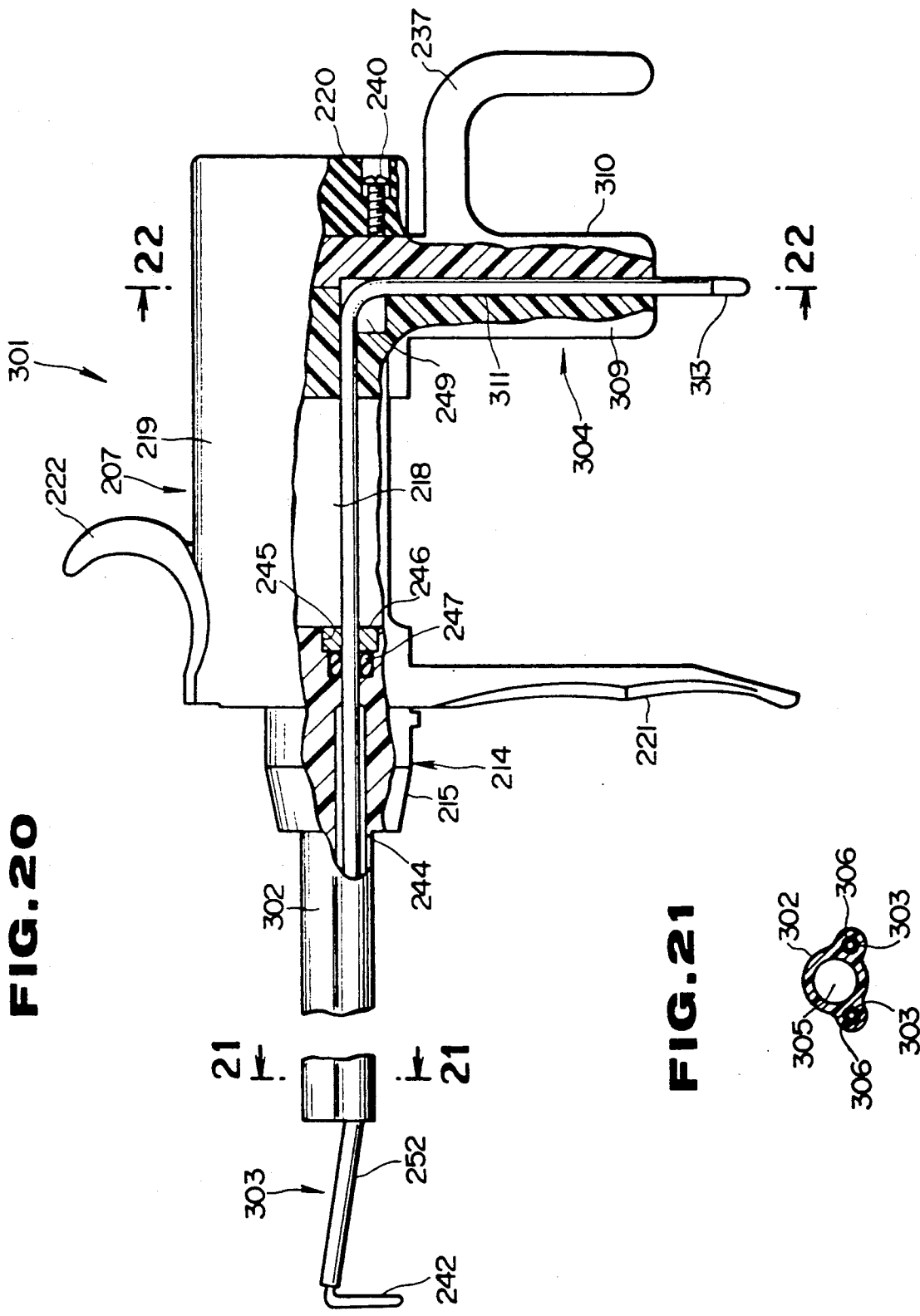
Figure 22:
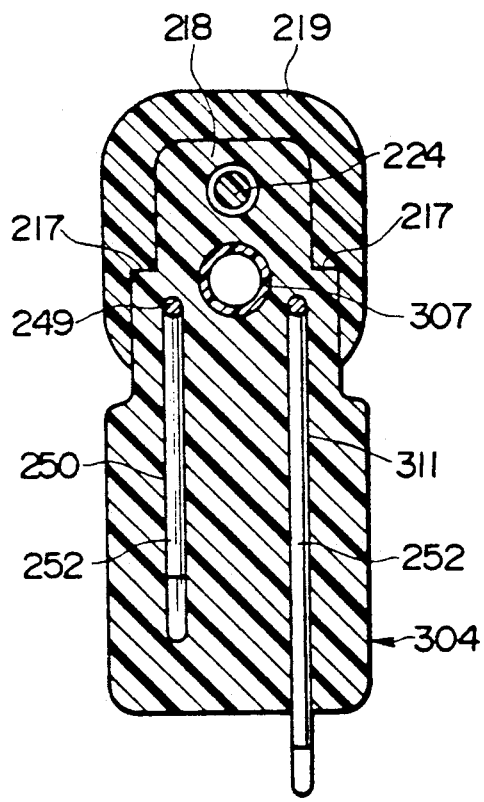
Figure 23:
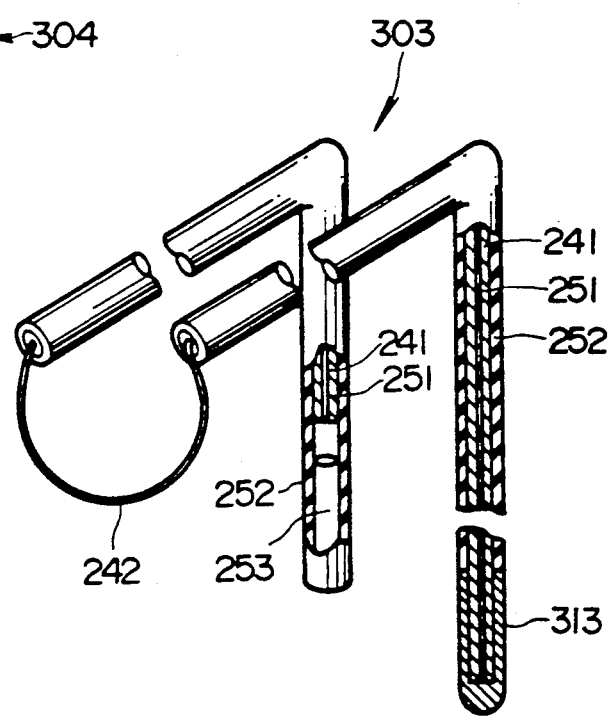

An operating part 301 in this embodiment is of substantially the same formation as of the operating part 201 of the third embodiment but is different in the respect that, as shown in FIG. 21, a guide tube 302 is a different shape pipe of plastics having an optical sighting tube inserting hole 305 and electrode inserting holes 306 and is projected as molded integrally with the body 207 with an electrode part 303 inserted through the electrode inserting holes 306 forward of the connecting part 214 of the body 207. Also, an insulating pipe 307 extended to the optical sighting tube connecting part 220 through the groove 218 of the body 207 from the connecting part 214 is molded of plastics integrally with the body 207.

Further, as shown in FIG. 20, the electrode part 303 in one axis is bent at right angles within the space 249 of the slider front part 309 of the slider part 304, is led downward and is projected downward from the lower end of the slider part 304 through a groove 311 formed to the lower end of the slider front part 309 and slider rear part 310 from the space 249 provided between the slider front part 309 and slider rear part 310.

A plug 313 made of a metal as conducted with the wire 241 is connected to the tip of the electrode part 303 projected from the above mentioned slider part 304. When the above mentioned plug 313 is removably connected with a connector 315 provided on the hand base side of a cord part 314, a high frequency current source not illustrated and the electrode part 303 will be able to be electrically connected with each other. The other formations of the resecting handle 301 are the same as in the third embodiment.

According to this embodiment, as the electrode and slider are made integral and the connecting part of the slider with the cord is arranged at the lower end of the slider and away from the optical sighting tube made of a metal material, the electric current will be able to be prevented from leaking. Further, there are advantages that, as there is no electrode fixing mechanism within the slider, the electrode is connected directly with the cord by the connector and there is no movable part, a contact failure by an operation failure can be prevented and, further, as the long cord can be separated from the resecting handle, it will be easy to wash and keep.

The other formations, operations and effects are the same as in the first embodiment.

FIGS. 24 to 37 show the fifth embodiment of the present invention.

In this embodiment, a resectoscope apparatus 401 comprises in combination an elongate hollow sheath 402, an operating part 403 removably fitted to the rear of the above mentioned sheath 402 and an optical sighting tube 404 for observation inserted through the above mentioned sheath 402 from the rear part of the above mentioned operating part 403.

Figure 24:
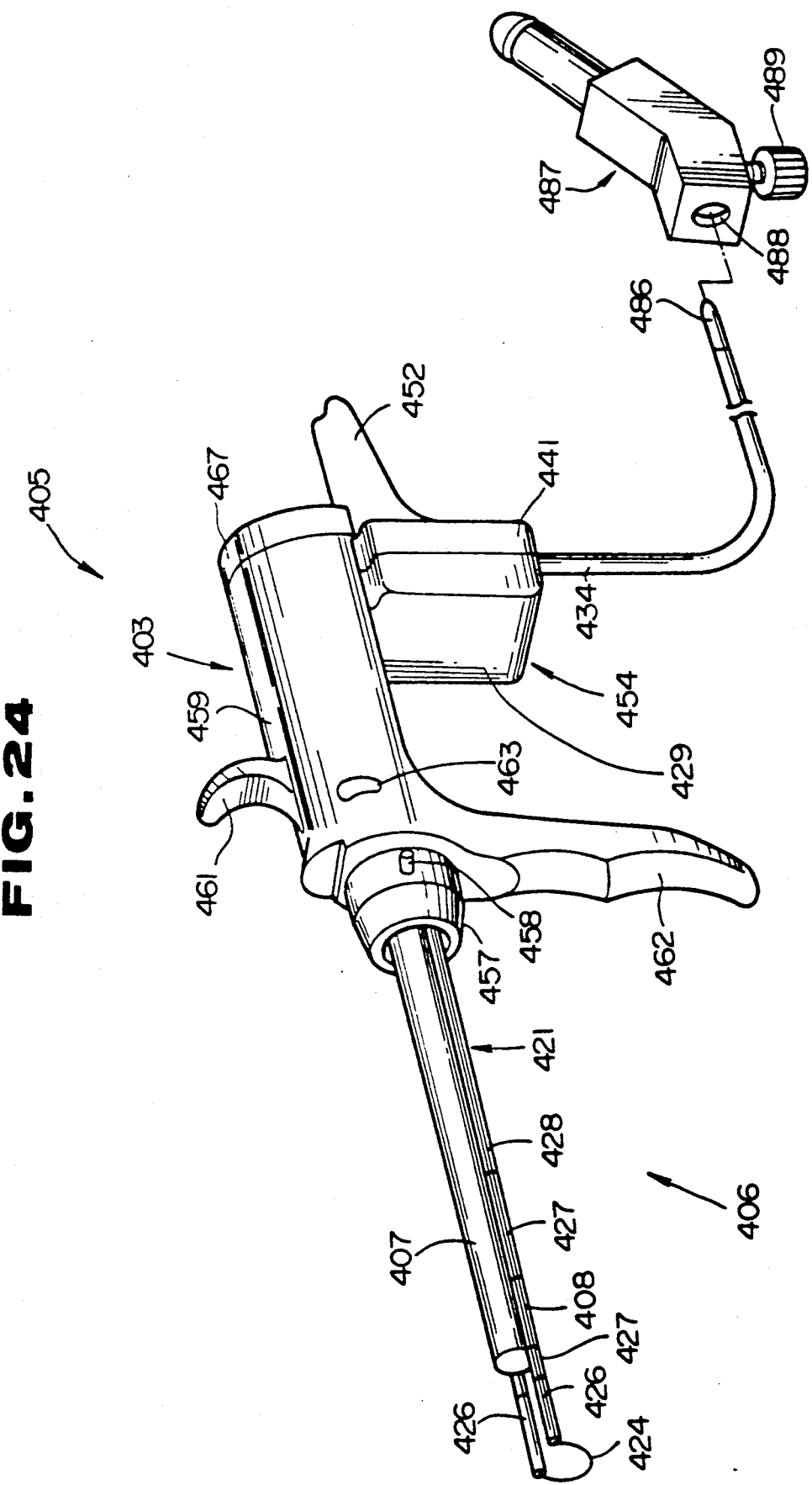
Figure 25:
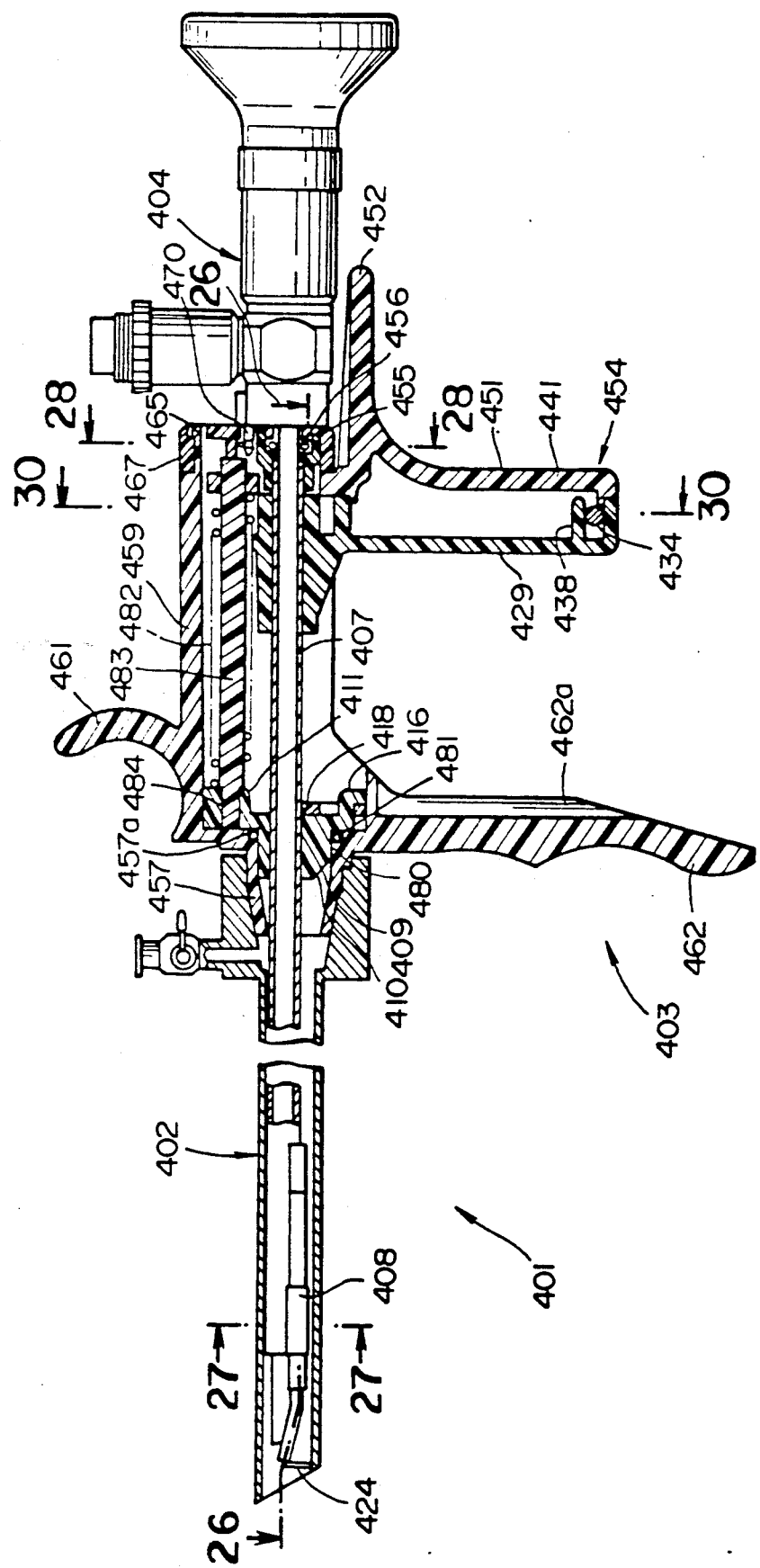
Figure 28:
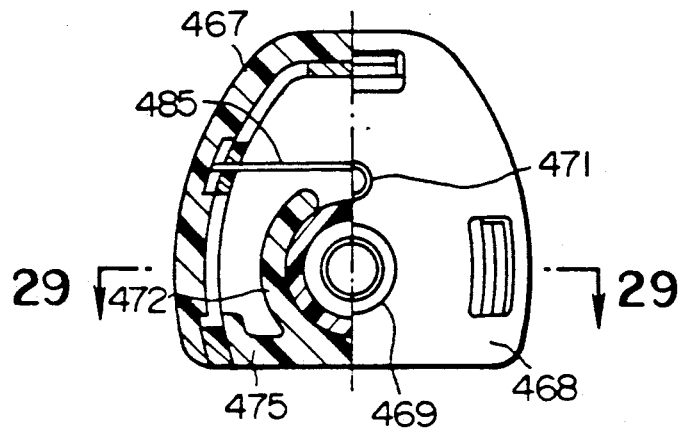

As shown in FIG. 32, the above mentioned operating part 403 is formed of an operating part body 405 and electrode unit 406. A stabilizer 408 made of such pipe member as is shown in FIGS. 24 and 27 is provided in the tip part of an elongate hollow guide tube 407 forming the above mentioned electrode unit 406 and having the above mentioned optical sighting tube 404 inserted through it. The above mentioned guide tube 407 is fitted in the intermediate part with a body connecting part 409 as by bonding and is provided in the rear end part with a slider 454.

Figure 34:
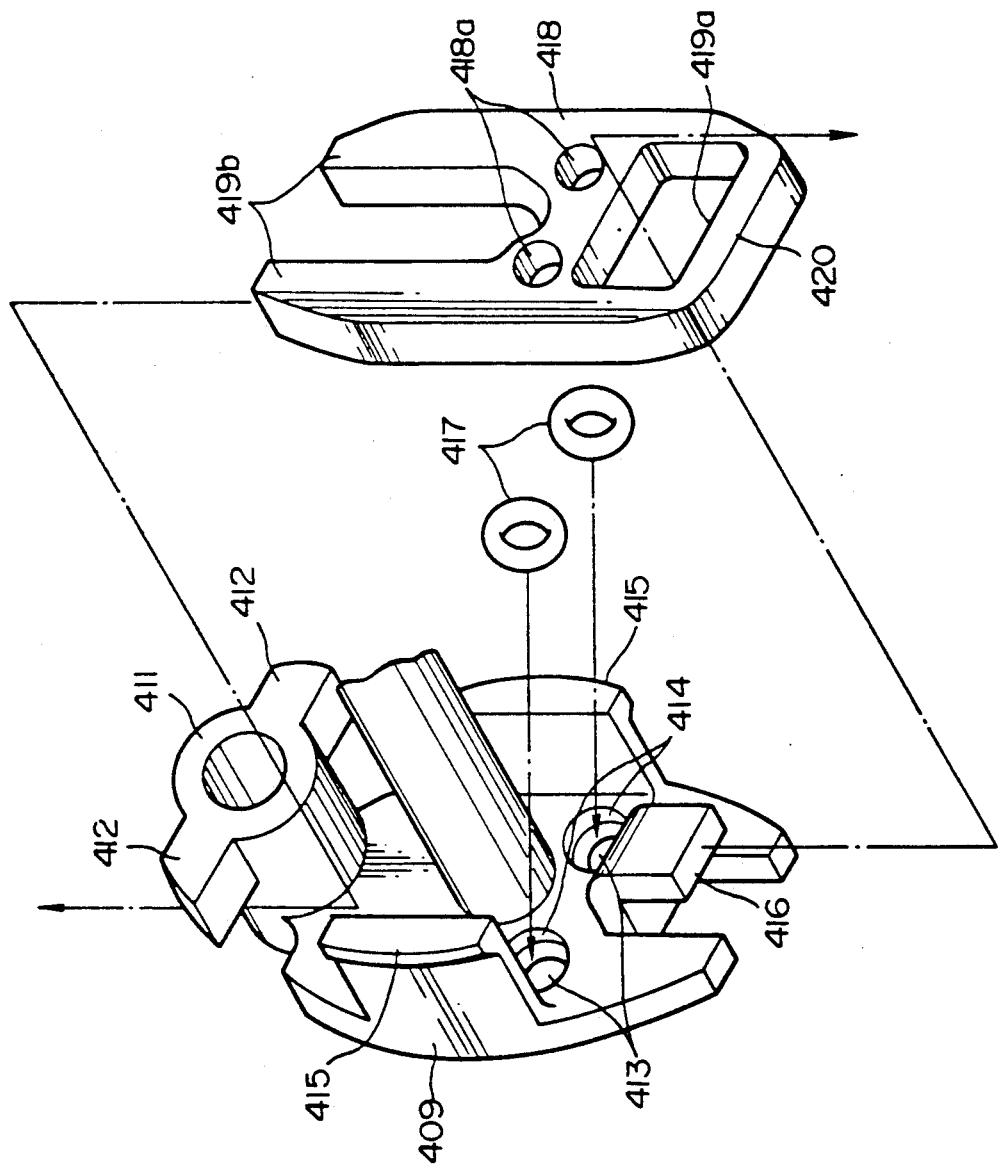

In FIGS. 32 and 34, the above mentioned body connecting part 409 is provided in the central part with a sleeve part 410 through which the above mentioned guide connecting part 409 and above the guide tube 407, a cylindrical spring shaft fitting part 411 having projections 412 on the right and left of the peripheral wall is provided to project. Electrode inserting holes 413 are provided on both sides below the guide tube 407. An O-ring groove 414 is annularly provided on the inner peripheral surface on the slider 454 side of each electrode inserting hole 413. Pawls 415 are provided to project on the slider 454 side on both right and left sides of the body connecting part 409 and a key-like projection 416 is provided to project below.

O-rings 417 are fitted respectively in the above mentioned O-ring grooves 414 and are fixed to the body connecting part 409 by an O-ring presser 418 which is plate-shaped and is provided with arm parts 419b made to hold the above mentioned guide tube 407 in the upper part, O-ring pressing holes 418a provided in the positions corresponding to the above mentioned electrode inserting holes 413 and fixing the above mentioned O-rings 417 in the electrode inserting holes 413 and a hole 419a in which the above mentioned key-like proportion 416 is to be inserted.

By the way, the O-ring presser 418 is fitted to the body connecting part 409 by inserting the key-like projection 416 into the hole 419a, is then slid upward and is fixed to the body connecting part 409 by pressing respectively the arms 419b with the projections 412 and the O-ring presser 418 at the lower end 420 with the key-like projection 416.

In the prior art, an O-ring is put into an O-ring groove and then a ring-shaped O-ring presser is inserted into the O-ring groove for bonding but, in this embodiment, no bonding is used and the assembly is made easy.

Figure 35:
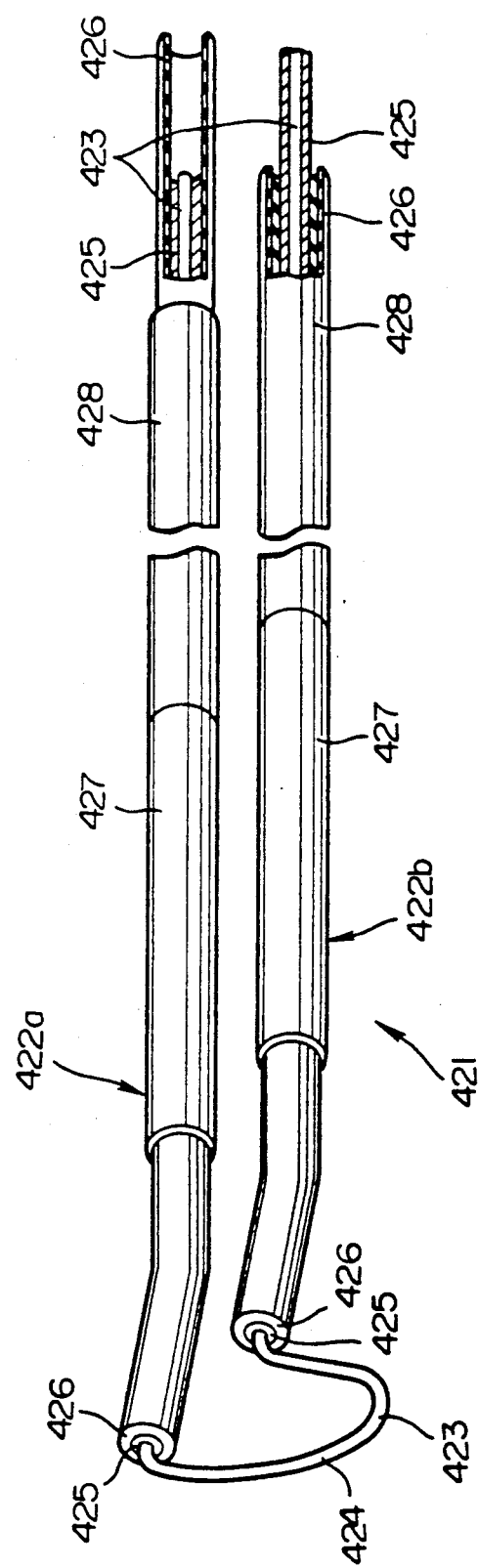

In FIG. 35, an electrode 421 inserted through the above mentioned electrode inserting holes 413, consists of two right and left shafts 422a and 422b parallel with each other and wires 423 are inserted respectively in the centers of the shafts. These wires 423 are projected on the tip sides out of the shafts 422a and 422b and are connected on the right and left with each other in the projected parts to form a semi-circular loop 424. Each of the shafts 422a and 422b is coated with an I-pipe 425 made of a pipe member coating the outer periphery of the wire 423 and further with an insulating tube 426 made of such insulating material as a resin on the outer periphery of the I-pipe 425. BY the way, the wire 423 and I-pipe 425 are cut so that the ends on the slider 454 side may be of substantially the same length. In one shaft 422a, the end surface is inside the rear end of the insulating tube 426. On the contrary, in the other shaft 422b, the end surface of the wire 423 and I-pipe 425 projects out of the end surface of the insulating tube 426.

O-pipes 427 are fixed as by calking to the above mentioned shafts 422a and 422b on the loop side. The O-pipe is determined in the length and fitting position so that, when the electrode 421 is incorporated into the operating part 403, in whatever position this electrode 421 may be operated, the stabilizer 408 will be positioned on the outer periphery of the O-pipe 427 and, even in case the electrode 421 is pulled in to the maximum, the O-pipe 427 will project at the end on the slider side out of the loop side end of the stabilizer 408. This O-pipe 427 prevents the insulating tube 426 from being hurt by the edge of the stabilizer 408 in case the electrode 421 slides on the inner periphery of the stabilizer 408 and serves to stiffen the electrode 421 in case it is projected forward. The shafts 422a and 422b on both sides are coated on the outer peripheries of the insulating tubes 426 and on the rear sides of the O-pipes with outer tubes 428 of insulating materials so that, in one shaft 422a, the insulating tube 426 may project out of the end surface of the outer tube 428 and, in the other shaft 422b, the end of the outer tube 428 may be substantially in the same position as of the insulating tube 426. Thus, by doubling the insulating tubes 426 and 428, the current leak from the electrode 421 can be reduced.

The shafts 422a and 422b of the thus formed electrode 421 are passed through the stabilizers 408 of the guide tube 407 from the tips and are then inserted through the electrode inserting holes 413 of the body connecting part 409.

The slider 454 in which the above mentioned electrode 421 is incorporated is formed of a front slider 429 and rear slider 441.

Figure 36:
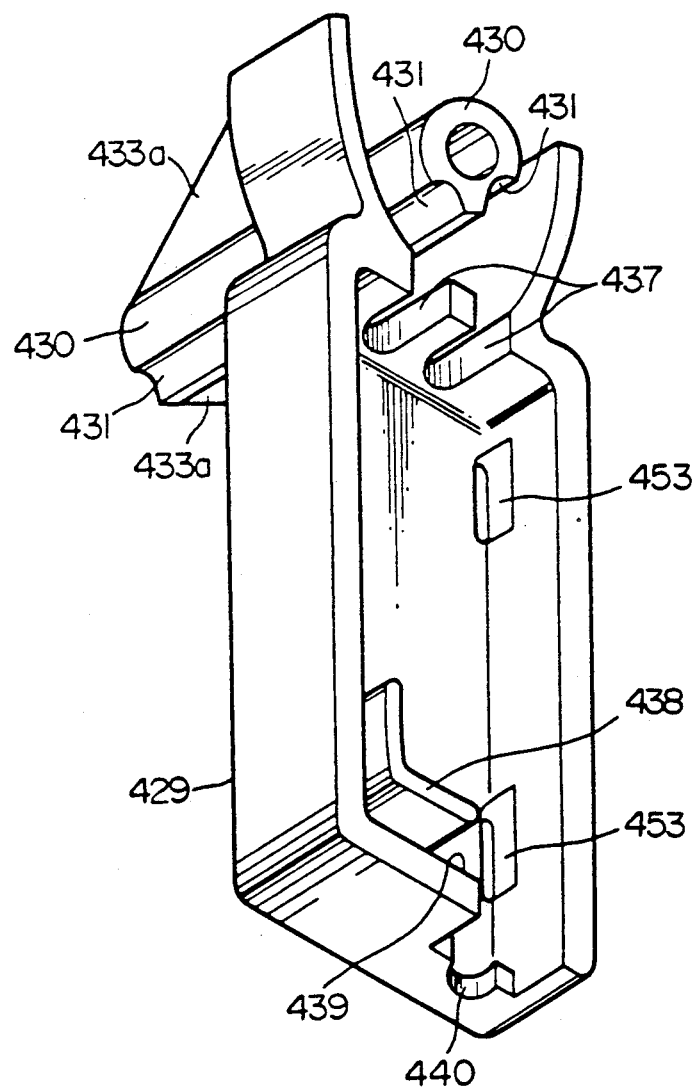
Figure 37:
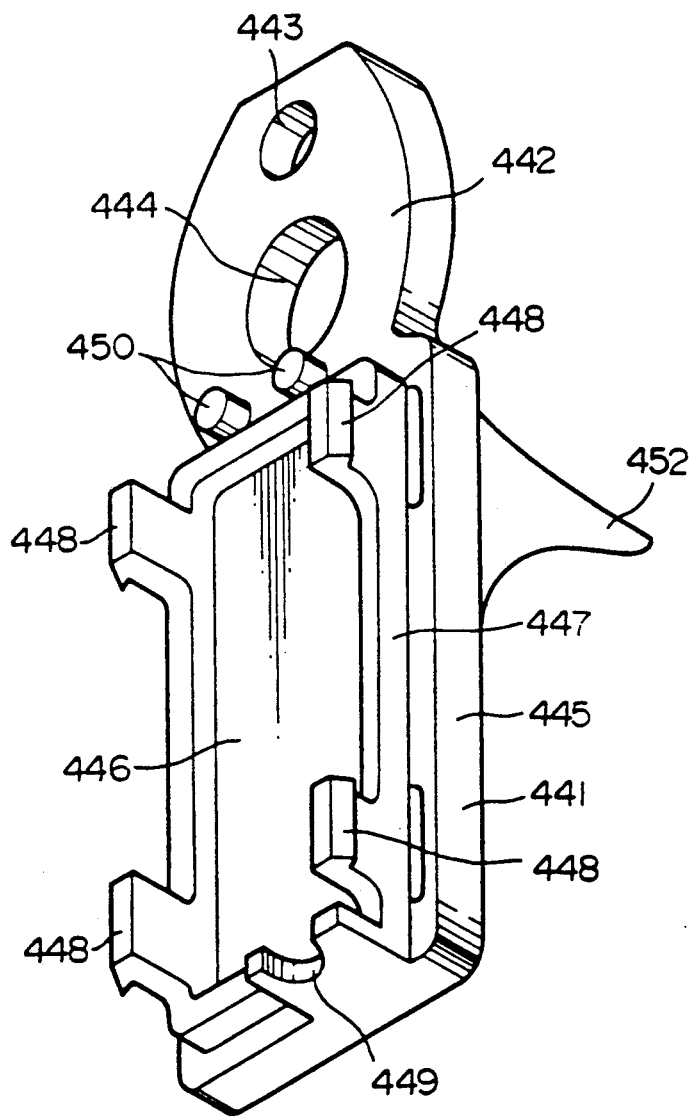

In FIG. 36, the front slider 429 forms curved surfaces on the upper side surfaces so as to be movably fitted into the later described operating part body 405, is rectangular in the lower part and is recessed inside. This front slider 429 is provided in the upper part with a cylindrical guide tube inserting part 430 and on both sides of the lower part of this guide tube inserting part 430 with electrode inserting grooves 431 and electrode inserting holes 432 (see FIG. 26) through which the shafts 422a and 422b of the electrode 421 can be inserted. This guide tube inserting part 430 is provided with three ribs 433a to increase the strength of the guide tube inserting part 430. The shafts 422a and 422b of the electrode 421 are inserted through the electrode inserting holes 432 along the electrode inserting grooves 431 of the guide tube inserting part 430 and are fitted to the front slider 429.

The shafts 422a and 422b of the electrode 421 inserted through the above mentioned front slider 429 and have bent portions are bent downward away from the sliding direction of the slider in a predetermined position 421a from the tip of the loop 424. In the case of bending this electrode 421a, as the operating part body 405 is not fitted, the dimension of the part to be bent will be easy to determine and the bending operation will be easy to carry out so that the bending work may be made in an accurate position.

Figure 30:
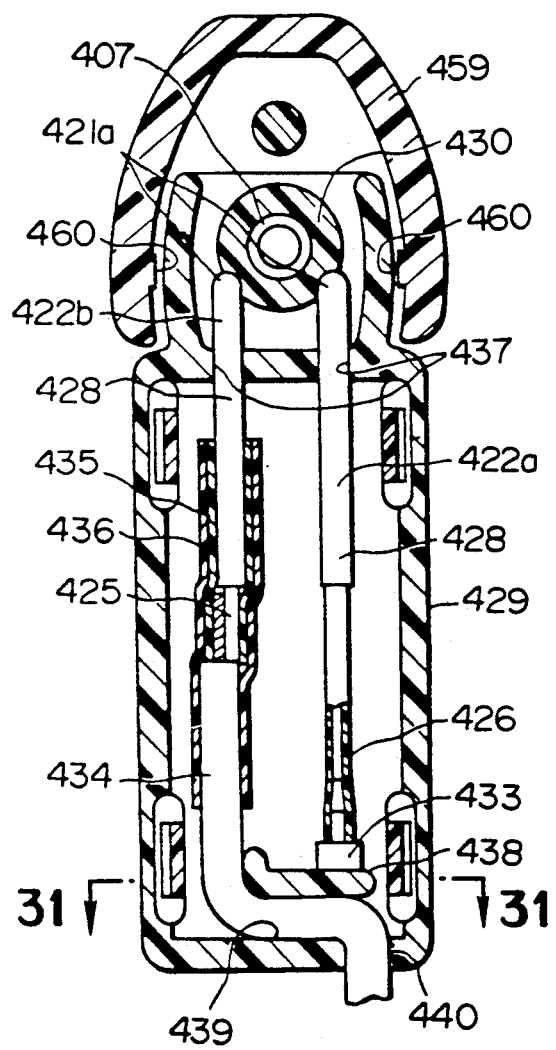

In FIG. 30, an embedded member 433 is pressed into the insulating tube 426 so as to keep watertightness at the rear end of the shaft 422a of the electrode 421 bent within the slider 454. An A-cord 434 is connected as by soldering to an I-pipe 425 projected from the rear end of the shaft 422b and this connecting part is doubly coated with thermocontracting tubes 435 and 436 so as to keep watertightness.

The thus incorporated shafts 422a and 422b are fitted at the rear ends into grooves 437 inside the front slider 429 and are contained within the front slider 429. An L-shaped projection 438 is provided within the front slider 429 to contact the embedded member 433 pressed into the rear end of the shaft 422a to prevent the removal of the embedded member 433. The above mentioned A-cord 434 is bent twice at 90 degrees, is passed between the projection 438 and lower wall surface 439 and is led at the tip out of a cord outlet 440. The A-cord 434 is thus arranged and therefore can be prevented from being removed when pulled downward.

Figure 31:
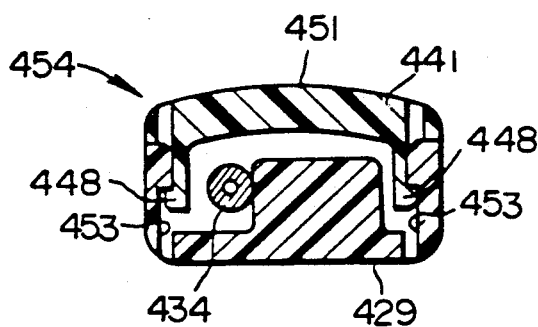

The rear slider 441 fitted to the above mentioned front slider 429 is formed to be of smooth curved surfaces on both side surfaces of the upper part 442, is provided on the upper side with a spring shaft inserting hole 443 and in the central part with a guide tube inserting hole 444 of a diameter larger than the outside diameter of the guide tube 407, is formed to be rectangular in the lower part 445 and is provided on the front surface 446 with ribs 447 which can be fitted as coinciding inside the front slider 429 and are provided with four pawls 448. The ribs 447 are provided on the lower surface with a cord presser 449 and on the upper surface with two cord pressers 450 to project. The rear surface 451 of the lower part 445 forms a slow curved surface as shown in FIG. 31 and a thumb hanger 452 extending rearward is provided above.

In case the front slider 429 and rear slider 441 are to be assembled, when the ribs 447 of the rear a slider 441 are fitted and pushed inside the front slider 429, the pawls 448 of the rear slider 441 will engage with the four recesses 453 provided inside the front slider 429 to combine the front slider 429 and rear slider 441 with each other as shown in FIG. 32.

In this case, the cord presser 449 will press the A-cord 434 passing through the cord outlet 440 and the cord pressers 450 will press respectively the shafts 422a and 422b of the electrode 421 fitted in the grooves 437a and therefore the A-cord 434 and electrode 421 will be fixed to the front slider 429 and rear slider 441.

Figure 29:
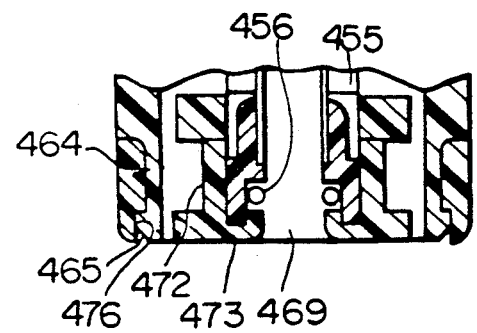

In FIG. 29, an O-ring setting member 455 is fitted by a bonding agent or sealant to the rear end of the above mentioned guide tube 407 and is like a cylinder which has a step difference in the inside diameter and outside diameter and in which the small diameter part on the outer periphery is somewhat smaller than the inside diameter of the guide tube inserting hole 444 of the rear slider 441 so that, when the operating part 403 is assembled, this small diameter part may be positioned within the guide tube inserting hole 444. The inside diameter of this small diameter part is made equal to the outside diameter of the guide tube 407 which is inserted and fixed in this position. The inner periphery of the other end part is of the inside diameter in which an O-ring 456 is inserted.

In the thus incorporated electrode unit 406, the slider 454 can freely slide in the axial direction around the guide tube 407 and, with this slider 454, the electrode 421 also move parallelly forward and rearward. That is to say, the projected amount of the loop 424 projected out of the guide tube 407 can be varied by the operation of the slider 454.

Figure 33A:
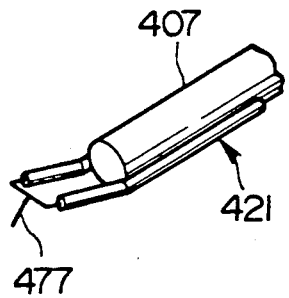
FIGS. 33(a)-33(c) are explanatory views of electrode tip parts.
Figure 33B:
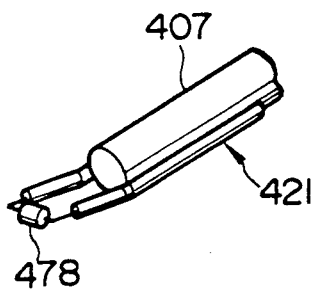
Figure 33C:
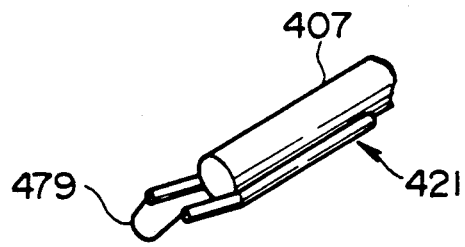

By the way, the electrode units 406 in which the electrodes formed in such knife type as is shown in FIG. 33(a), such roller type as is shown in FIG. 33(b) and such oblique loop type as is shown in FIG. 33(c) are incorporated are prepared and can be selected and incorporated in the operating part bodies 405 to make various types of operating parts 403.

On the other hand, a hollow tapered part 457 for removably fitting the sheath 402 is provided in the tip part of the above mentioned operating part body 405 forming the operating part 403. The above mentioned body connecting part 409 through which the electrode 421 of the electrode unit 406 and the guide tube 407 are inserted is connected within this tapered part 457.

By the way, this tapered part 457 must be kept water-tight when connected with the sheath 402 and therefore requires a strict dimensional precision. However, as this part is made hollow, in case it is made of plastics as by injection molding, the thickness will be able to be made constant and the variation of the dimensions by the contraction or extension at the time of injection molding will be able to be prevented.

The above mentioned tapered part 457 is provided at the rear end of the inner surface with an O-ring groove 457a fitted with an O-ring 481 and on both right and left sides of the outer surface with connecting pins 458 to project. A cover 459 is extended in the rear of this tapered part 457. As shown in FIG. 30, the upper part 442 of the rear slider 441 is formed to be of such cross-sectional shape as is freely movable in the lengthwise direction within the cover 459. Projections 460 contacting the side surfaces as sliding surfaces of the upper part 442 of the rear slider 441 are provided in the lengthwise direction on both sides of the inner surface of the cover 459 so that the contact area of the of the inner surface of the cover 459 with the side surface of the slider 454 may be reduced and the movement of the slider 454 within the cover 459 may be made smooth.

Further, an upper finger hanger 461 and lower finger hanger 462 are provided respectively forward above and below on the outer periphery of the cover 459 and this upper finger hanger 461 is positioned a little rearward of the lower finger hanger 462. BY this position relation, the ease of holding the operating part 403 is improved. Ribs 462a of a thickness of about 3 mm. are provided on both right and left sides on the rear surface of the lower finger hanger 462 to increase the strength of the lower finger hanger 462.

Further, rectangular through holes 463 engaged with the pawls 415 provided in the above mentioned body connecting part 409 are provided on both sides of the front part of the cover 459. A small diameter part 464 formed by a step is extended in the rear part of the cover 459, three pawls 465 are provided on the upper surface and side surface sides of the rear end part and pin holes 466 are provided on the right and left sides.

After the electrode unit 406 is fitted to the operating part body 405, a cap member 467 is fitted to the above mentioned small diameter part 464. An optical sighting tube inserting hole 469 and a pin hole 471 for inserting a connecting pin 470 for connecting the optical sighting tube 404 are provided on the rear surface 468 of this cap member 467. Also, a rib 472 and groove 473 which can fit the above mentioned O-ring setting member 455 and a supporting rib 475 supporting the side wall of the operating part body 405 so as not to be inside when fitted to the operating part body 405 are provided inside. A total of three recesses 476 engaging the pawls 465 of the operating part body 5 are provided on the inside upper surface and lower surface.

A small diameter part 484 provided in the tip part of a spring shaft 483 is fitted and fixed in the spring shaft fitting part 411 provided in the above mentioned body connecting part 409. The spring shaft 483 passes at the rear end through the spring shaft inserting hole 443 provided in the above mentioned rear slider 441, contacts the inner surface of the cap member 467 and is inserted through a coiled spring 482 which is incorporated as energized by the rear end surface of the above mentioned spring shaft fitting part 411 and the front end surface of the rear slider 441.

The method of assembling the operating part body 405 and electrode unit 406 shall be described in the following. First of all, the O-ring 481 is fitted to the O-ring fitting part 480 of an inside diameter equal to the inside diameter of the tapered part 457 of the operating part body 405 provided in the root part of the sleeve 410 of the body connecting part 409. The water leak between the operating part body 405 and body connecting part 409 will be prevented by this O-ring 481. The spring 482 is pressed and contracted to some extend and is inserted between the spring shaft fitting part 411 of the body connecting part 409 and the upper part 442 of the rear slider 441 so that the end surface of the spring 482 may be in the position of the shaft inserting hole 443. By the way, the inside diameter of the spring 482 is made larger than the inside diameter of the spring shaft inserting hole 443 so that the spring 482 may not spring out of the spring shaft inserting hole 443. Then, the spring shaft 483 of a diameter smaller than the inside diameter of the spring shaft inserting hole 443 is inserted through the spring shaft inserting hole 443 and spring 482 from the rear of the upper part 442 of the rear slider 441 and the small diameter part 484 at the tip of the spring shaft 483 is inserted into the spring shaft fitting part 411 of the body connecting part 409. Also, the O-ring 456 is fitted in the O-ring setting member 455.

The, the electrode unit 406 assembled as mentioned above is fitted in to insert the guide tube 407 through the tapered part 457 from the rear of the operating part body 405. Then, the pawls 415 of the body connecting part 409 will engage with the holes 463 of the operating part 405 to combine the operating part body 405 and electrode unit 406 with each other. (See FIG. 26). After the pins 485 are inserted through the pin holes 466 on the right and left of the small diameter part 464, the cap member 467 is fitted into the small diameter part 464 of the operating part body 405. When the pawls 465 of the operating part body 405 engage with the recesses 476 of the cap member 467, the cap member 467 will be fixed to the operating part body 405. The O-ring 456 is fixed as held by the O-ring setting member 455 and cap member 467. This O-ring 456 is fitted by the same simple method as of fitting the above mentioned O-ring 417 to contribute to the reduction of the assembling time.

By the way, as the cap member 467 is connected to the operating part body 405 and the pin 485 is covered from outside, the pin 485 will not drop, the bonding so far used to fix the pin will be able to be eliminated and the assemblability of this part will be improved. Also, the spring shaft 483 is held between the body connecting part 409 and cap member 467 and is incorporated without bonding. Further, if the outside diameter of the small diameter part 484 is made smaller than the inside diameter of the spring shaft fitting part 411 of the body connecting part 409, the spring shaft 483 will be able to move more or less vertically and horizontally and, even in case the slider 454 is twisted or is swung vertically and horizontally, it will not bite into the spring shaft inserting hole 443 of the rear slider 441. Thus, the operating part 403 is assembled.

A mouthpiece 486 is fitted to the tip part of the above mentioned A-cord 434 and can be fixed by an inserting screw 489 to a mouthpiece inserting part 488 of an adapter 487.

By the way, in the resectoscope apparatus 401 shown in this embodiment, such main component parts as the operating part body 405, body connecting part 409, O-ring presser 418, front slider 429, rear slider 441, O-ring setting member 455, cap member 467 and spring shaft 483 are formed of plastics by injection molding.

The method of using the resectoscope apparatus 401 in this embodiment shall be described in the following.

First of all, the sheath 402 in which a mandolin not illustrated is inserted is inserted into a body cavity, for example, into a bladder through a urethra. After the mandolin is removed, the operating part 403 combined with the optical sighting tube 404 is inserted into the sheath 402. When the pin 485 of the operating part 403 is engaged with the groove of the connecting pin 470, the optical sighting tube 404 will be removably fixed to the operating Part 403. In this case, the adapter 487 fitted to the A-cord 434 of the operating part 403 will be connected to a high frequency cauterizing current source apparatus not illustrated and the light guide connected to a light source apparatus not illustrated will be connected to the optical sighting tube 404.

Now, the first finger is hung on the upper finger hanger 461, the thumb is hung on the thumb hanger 452 and the other fingers are hung on the lower finger hanger to hold the resectoscope apparatus 401. In this state, the slider 454 is energized rearward by the spring 482 and the loop 424 of the tip part of the electrode 421 is retracted into the sheath 402.

Next, while confirming the visual field with the optical sighting tube 404, the slider 454 is pushed out forward with the thumb and the loop 424 is pressed against a part to be resected. While feeding a high frequency cauterizing current to the loop 424, if the force of the thumb is released, the slider 454 will be pushed back by the spring 424 and at the same time the loop 424 will be pulled into the sheath 402 while resecting the tissue.

In this embodiment, as the electrode unit 406 is assembled and is then incorporated into the operating part body 405, the position of the electrode 421 can be accurately determined and it is not necessary to provide an electrode 421 position adjusting means. Therefore, the parts can be made few and the cost can abe reduced.

In the resectoscope apparatus 401 shown here, the electrode 421, slider 454 and A-cord 434 are made integral, an electric connecting part is eliminated, many parts are formed of insulating materials, the electric safety is very high and the assemblability is also elevated.

By the way, in this embodiment, the A-cord. 434 is made integral with the slider 454 but may be removably fitted to the slider 454 and many parts are formed of plastics but may be formed of such other materials as metals and ceramics. Further, the body connecting part 409 and cap member 467 are assembled in the snap fitting system utilizing the resiliency of plastics but may be attached by bonding, soldering or screwing.

Figure 38:
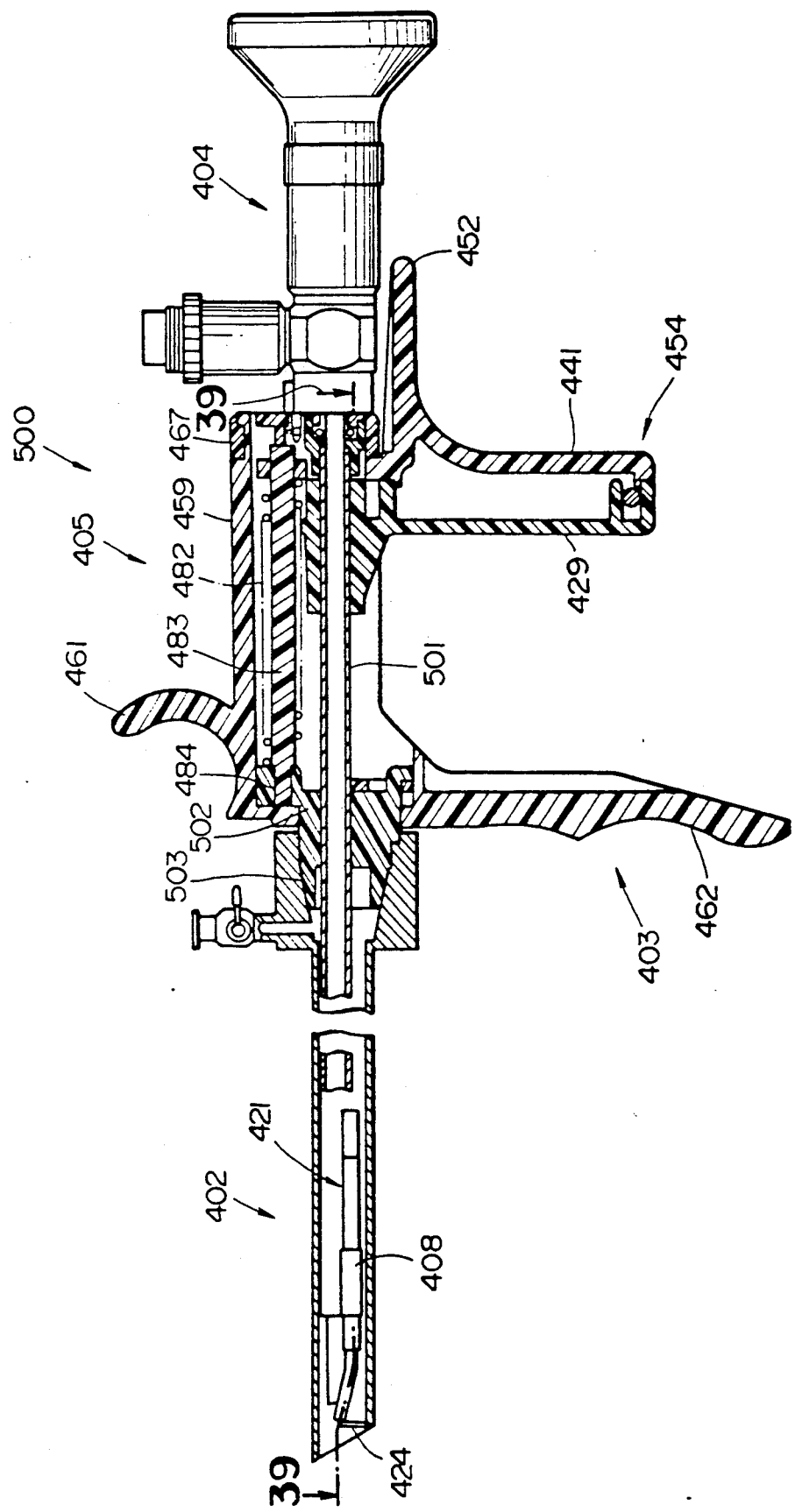
FIGS. 38 and 39 relate to the sixth embodiment of the present invention.
Figure 39:
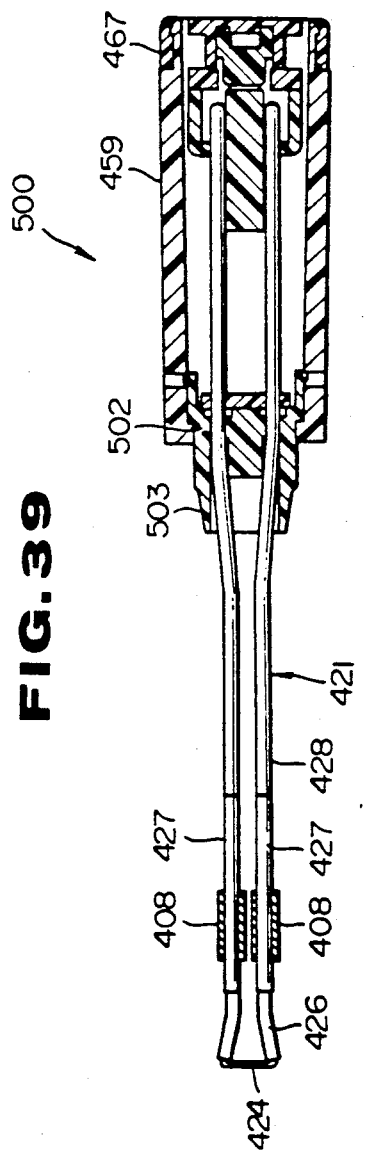

FIGS. 38 and 39 show the sixth embodiment of the present invention.

In this embodiment, a body connecting part 502 and a tapered part 503 for connecting the sheath 402 are made integral. The formations of the other parts are the same as in the fifth embodiment, shall bear the same reference numerals and shall not be explained.

In the resectoscope apparatus in the present invention including the fifth embodiment, the part important to determine the position relation of the sheath and operating part is the tapered part. Therefore, the easier to determine the position relation of the tapered part and the tip part of the electrode, the easier to accurately set the distance between the electrode tip and sheath tip.

A body connecting part 502 of a resectoscope apparatus 500 of this embodiment has a tapered part 503 passing through the front end surface of the operating part body 405. This tapered part 503 can removably connect the sheath 402. The other formations are the same as in the fifth embodiment.

In the resectoscope apparatus 500 in this embodiment, as the body connecting part 502 is provided with the tapered part 503, there is an advantage that the tapered part 503 and the tip part of the electrode unit 406 can be positioned more easily and accurately than in the fifth embodiment.

The other effects are the same as in the fifth embodiment.

Figure 40:
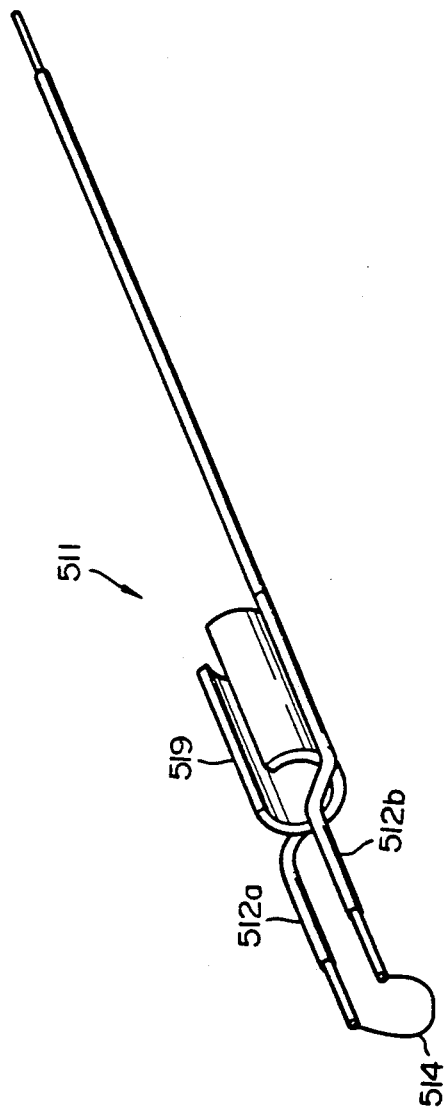
FIGS. 40 to 42 relate to the seventh embodiment of the present invention.
Figure 41:
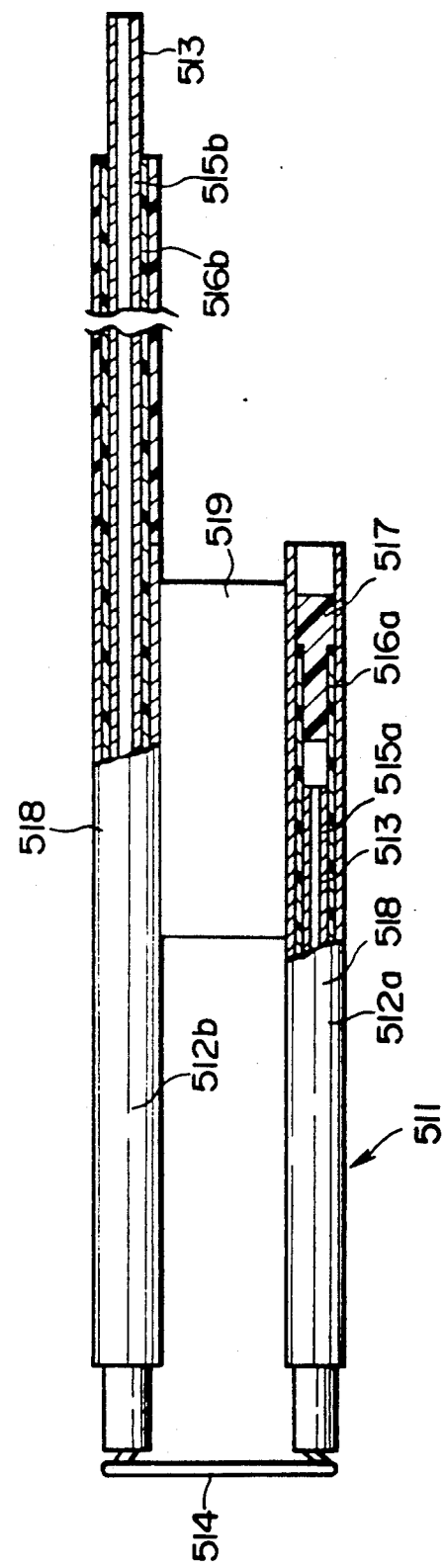
Figure 42:
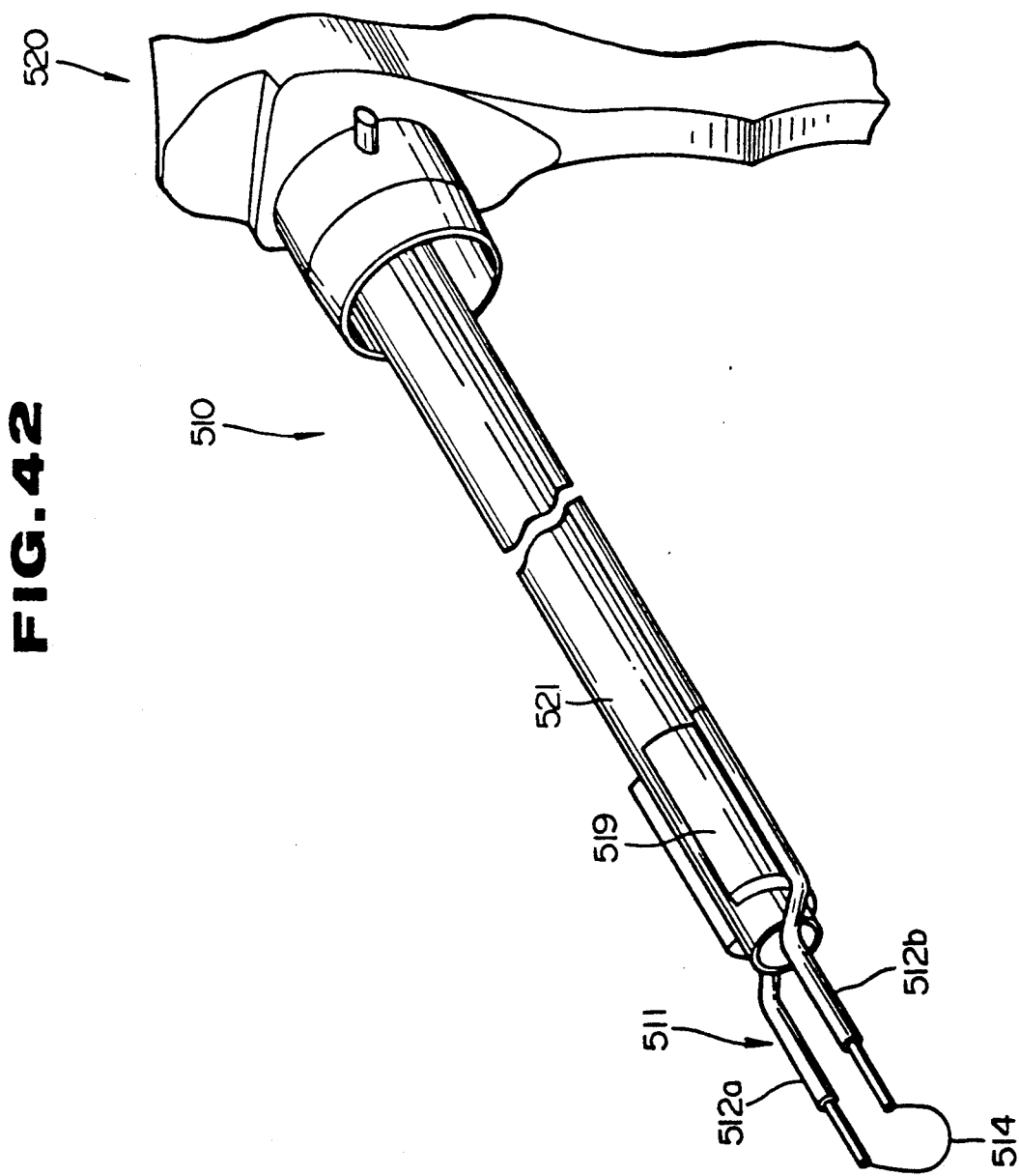
Figure 43:
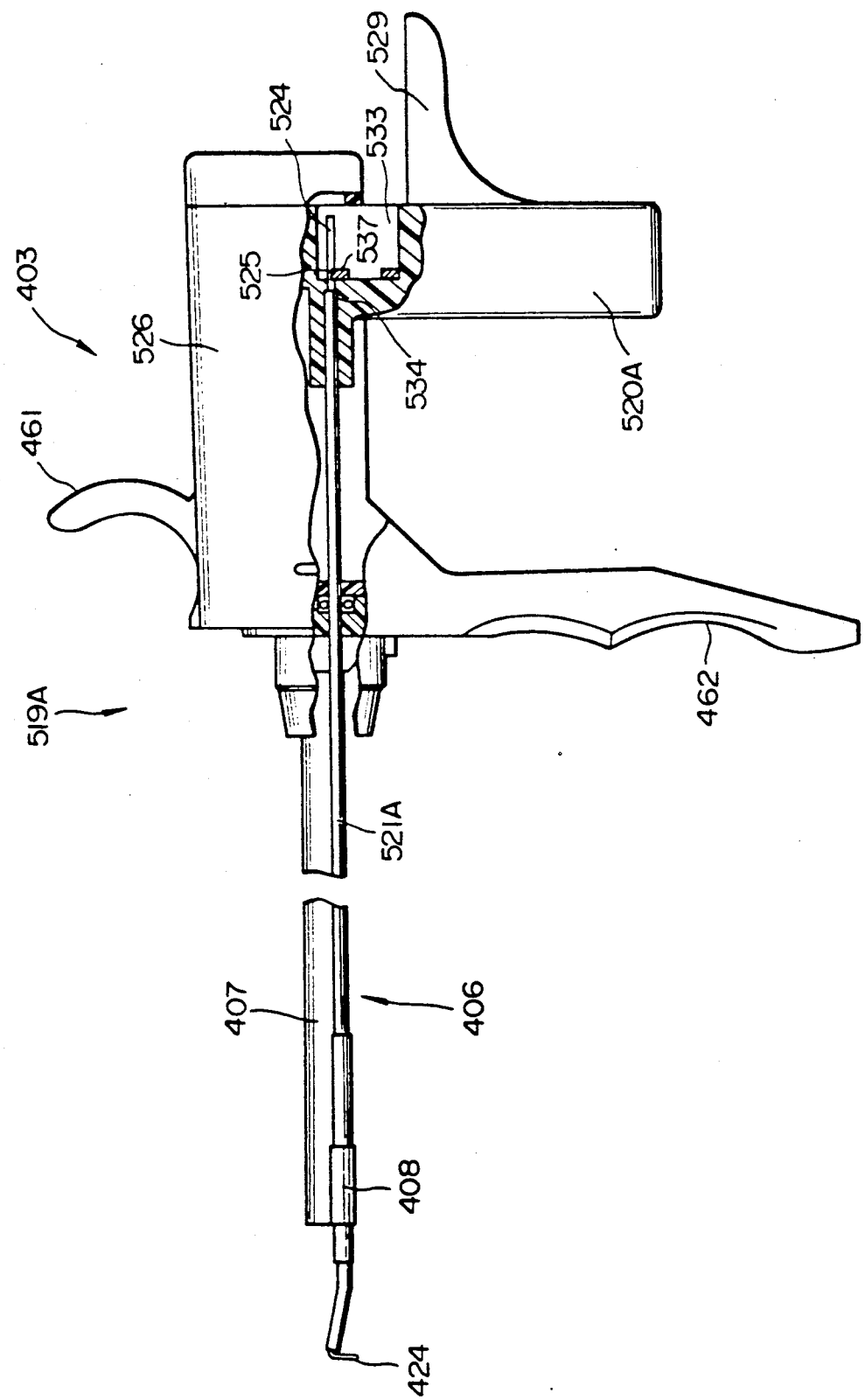
FIGS. 43 to 47 relate to the eighth embodiment of the present invention.

FIGS. 40 to 42 show the seventh embodiment of the present invention.

In this embodiment, an electrode 511 consists of two right and left shafts 512a and 512b parallel with each other through which wires 513 are inserted in the respective centers. These wires 513 project out of the ends on one side of the shafts 512a and 512b and are connected on the right and left in the projecting parts so as to be a semi-circularly formed loop 514. The wires 513 are coated on the outer peripheries respectively with I-pipes 515a and 515b and further on the outer peripheries respectively with insulating tubes 516a and 516b made of such insulating material as a resin.

By the way, the wires 513 and I-pipes 515a and 515b are cut at the rear ends so as to be substantially of the same length. In the shaft 512a, its end surface is inside the rear end of the insulating tube 516. On the contrary, in the shaft 512b, the end surfaces of the wire 513 and I-pipe 515b project out of the end surface of the insulating tube 516b. An embedded member 517 coated with a bonding agent or sealant is fitted to the insulating tube 516a at the rear end so as to keep watertightness. Further, the insulating tubes 516a and 516b are coated on the outsides respectively with O-pipes 518 which are fixed by soldering or laser welding in symmetrical positions to a cylindrical guide pipe 519 partly cut off on the outer periphery.

By the way, in the shaft 512a, the wire 513, I-pipe 515 and insulating tube 516a are cut to be of such length that the embedded member 517 may be inside the O-pipe 518 but, in the shaft 512b, the wire 513, I-pipe 515b and insulating tube 516b are extended rearward and this shaft 512b is fixed to a slider not illustrated. The shafts 512a and 512b in the parts projected forward from the guide pipes 519 are once obliquely bent upward and are bent so as to be in the original axial direction. The respective pipes and tubes will be prevented by these two bent parts from being pulled out or removed. The same as in the fifth embodiment, electrodes of tip parts of various shapes are prepared.

FIG. 42 shows the electrode 511 as incorporated in the operating part 520.

The operating part 520 is substantially the same as is shown in the fifth and sixth embodiments but is different in respect that one electrode inserting hole 413 is provided in each of the body connecting parts 409 and 502 and a stabilizer 408 is provided in the tip part of a guide tube 521.

The method of assembling a resectoscope apparatus 510 of this embodiment is the same as in the fifth embodiment after a guide tube 521 is inserted through a guide pipe 519.

In the resectoscope apparatus 510 in which the electrode 511 is incorporated, with the forward and rearward movement of the slider, while the electrode 511 is moving forward and rearward, the guide pipe 519 will slide on the outer periphery of the guide tube 521. That is to say, the electrode 511 can be moved stably by the guide pipe 519.

The great feature of this embodiment is that only the shaft 512b of the two shafts 512a and 512b of the electrode 511 is connected to the slider 454.

Generally, in a resectoscope apparatus, a high frequency cauterizing current unavoidably leaks from the electrode to the sheath and operating part and there is a danger that, in case a large current leaks, the operator and patient will be burned. It has been experimentally made clear that the current leak from a one-shaft electrode is smaller than from a two-shaft electrode. Therefore, in the resectoscope apparatus 510 in this embodiment, there are effects that the current leak is reduced and the electric safety is elevated.

The other formations, operations and effects are the same as in the fifth embodiment.

FIGS. 43 to 47 show the eighth embodiment of the present invention.

The operating part 403 of a resectoscope apparatus 519A in this embodiment is different with respect to the structure of a slider 520A, the method of connecting an electrode 521A with the slider 520A and the removable type of an A-cord 522 but is the same otherwise as in the fifth embodiment.

Figure 45:
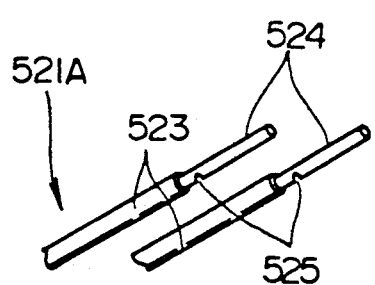
Figure 46:
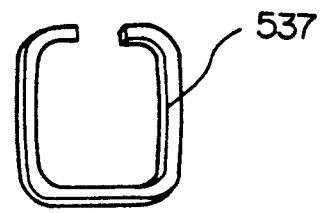
Figure 47:
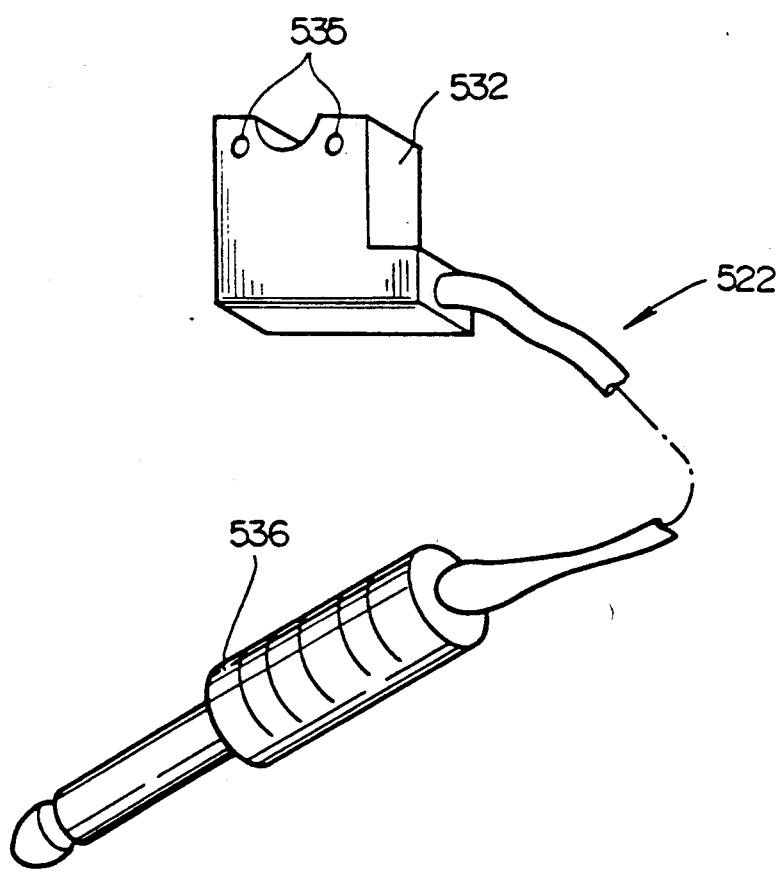
Figure 48:
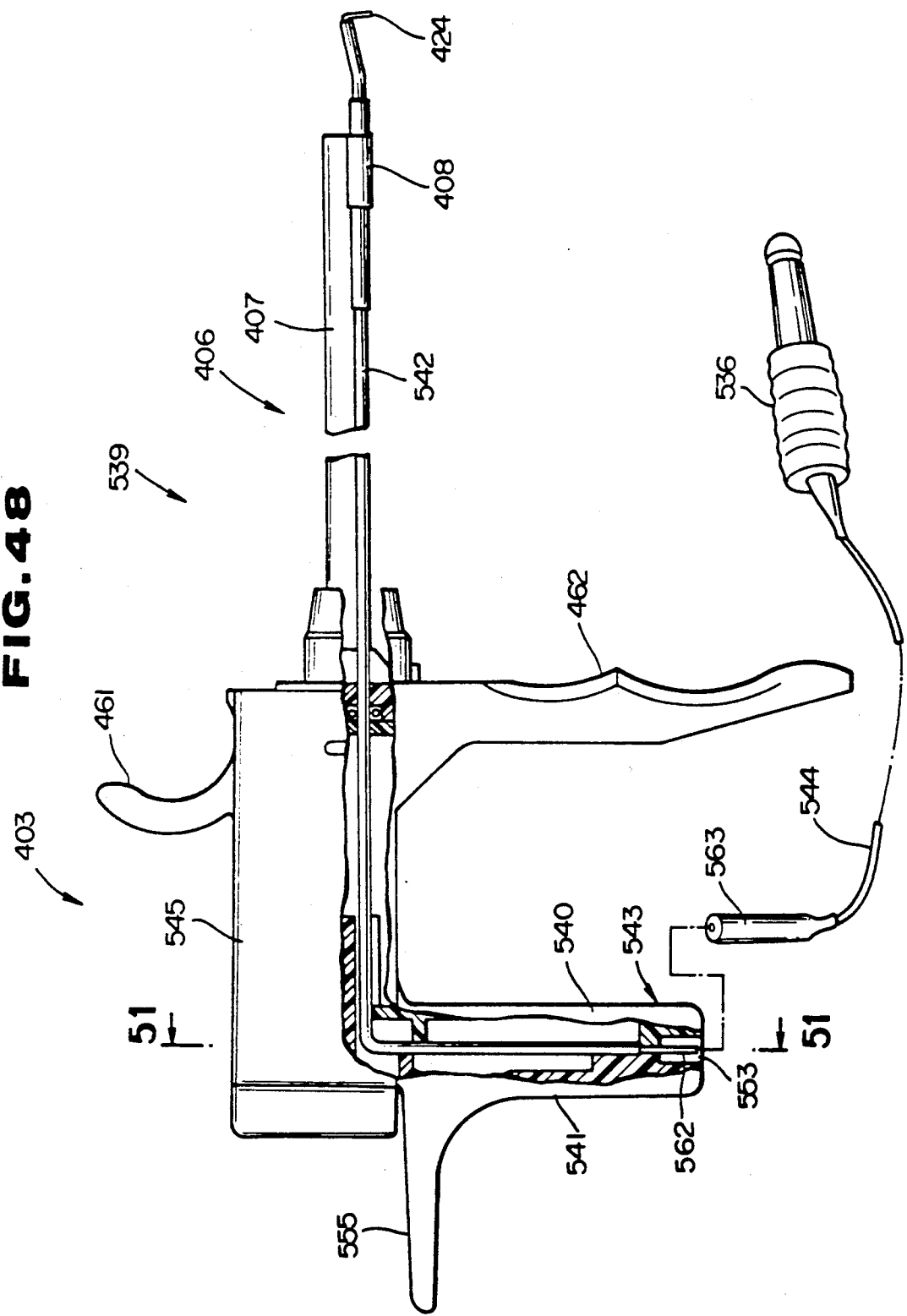
FIGS. 48 to 51 relate to the ninth embodiment of the present invention.
Figures 49, 50:
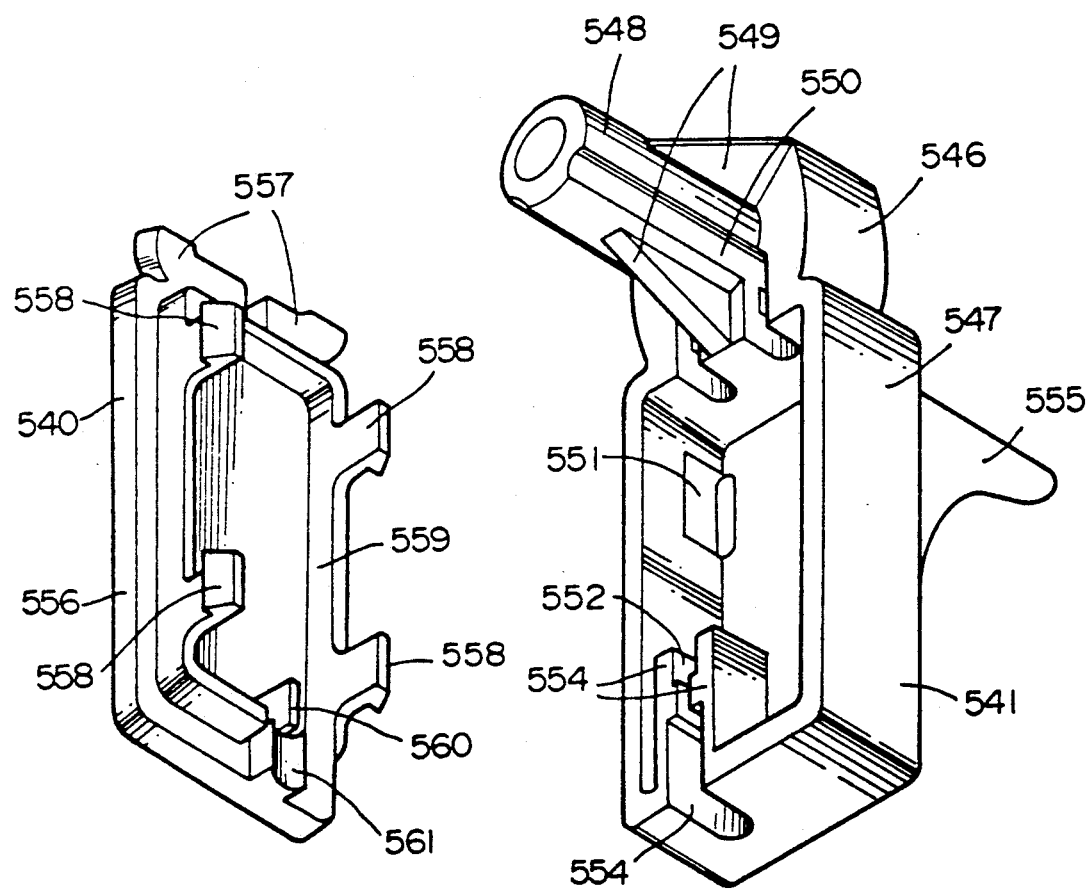
Figure 51:
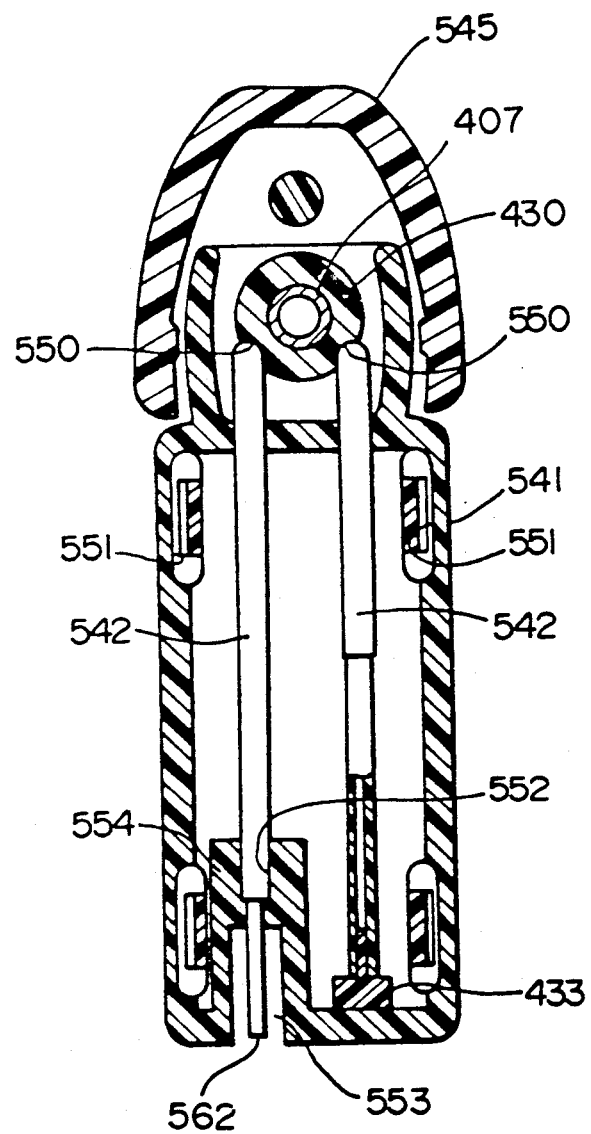

In the rear end part of the electrode 521A, as in FIG. 45, on both sides, I-pipes 524 project from insulating tubes 523 and are provided on the lower sides with incisions 525.

Figure 44:
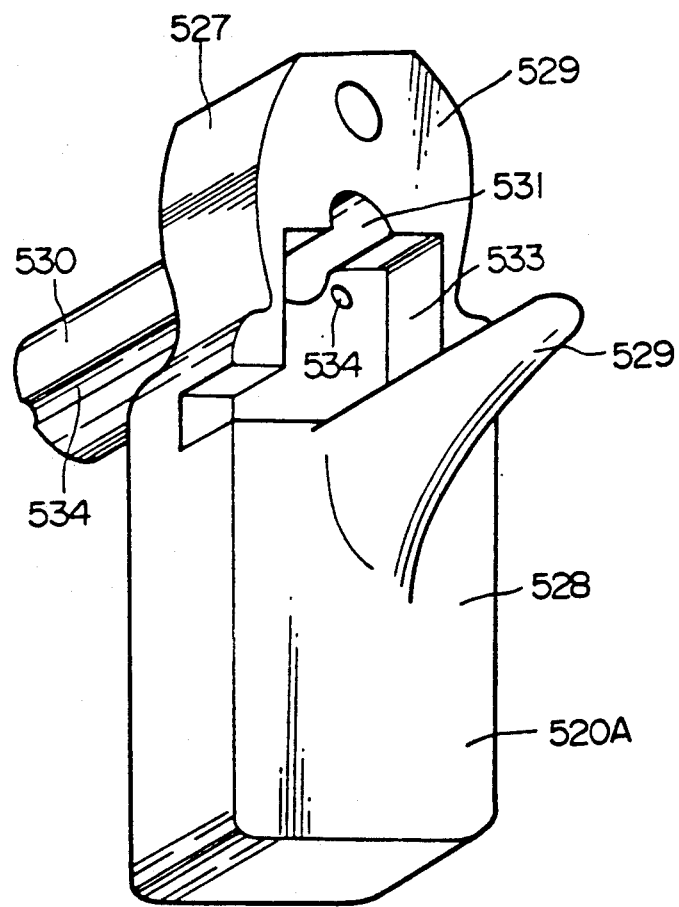

As shown in FIG. 44, the slider 520A consists of an upper part 527 in which the side surfaces to be inserted inside an operating part body 526 form curved surfaces and a rectangular lower part 528 provided on the rear surface with a thumb hanger 529. The upper part 527 is provided on the front surface with a cylindrical guide tube inserting part 530 and a guide tube inserting hole 531 passing through this guide tube inserting part 530 and the upper part 527. On the hand base side end surface of the slider 520A is provided an A-cord connecting part 533 which is an opening in which a slider connecting part 532 of the A-cord 522 shown in FIG. 47 can be inserted. Further, electrode inserting holes 534 in which the electrode 521A can be inserted at the rear ends through the guide tube inserting part 530 and upper part 527 are provided parallelly on both lower sides of the guide tube inserting hole 531.

Electrode inserting holes 535 in which the electrode 521A can be inserted at the rear ends are provided in the slider connecting part 532 of the A-cord 522. A plug 536 connectable to a current source apparatus not illustrated is provided at the other end of the A-cord 522.

In connecting the electrode 521A with the slider 520A, the electrode 521A is inserted at the rear ends into the electrode inserting holes 534 from the front surface side of the slider 520A and then a C-ring 537 made of a spring member is fitted deep in the A-cord connecting part 533. Then the C-ring 537 will fit in the incisions 525 at the rear ends of the electrode 521A and the electrode 521A and slider 520A will be connected with each other. By the way, such sealant as silicone rubber is injected into the clearance between the electrode inserting hole 534 and the shaft of the electrode 521 to keep watertightness.

In the case of making a treatment by using the operating part of this embodiment, the slider connecting part 532 of the A-cord 522 is connected to the A-cord connecting part 533 of the slider 520A and the I-pipes 524 at the rear ends of the electrode 521A are inserted into the electrode inserting holes 535: of the slider connecting part 532 so that the electrode 521A and A-cord 522 may be electrically connected with each other.

The other using methods are the same as in the fifth embodiment.

In the operating part according to this embodiment, the assembly of the electrode and slider is simpler than in the fifth embodiment. In case the operating part in the fifth embodiment is used, during the treatment, if the electrode tip part is to be changed (for example, from the loop type to the roller type), as the A-cord is fitted to the operating part, the A-cord must be pulled out of the current source apparatus to replace the operating part. However, the operator can not touch the adapter and cord on the current source apparatus side in the insanitary zone and the assistant must pull out and connect the cord. In such case, as the operating part in this embodiment is removably fitted with the A-cord, the operator himself can replace only the operating part efficiently.

The other formations, operations and effects are the same as in the fifth embodiment.

FIGS. 48 to 51 show the ninth embodiment of the present invention.

The operating part 403 of a resectoscope apparatus 539 of this embodiment is the same as in the fifth embodiment except the structure of a front slider 540 and rear slider 541, the method of connecting an electrode 540 with a slider 543 and the removable fitting of an A-cord to the operating part.

The slider 543 is formed of the front slider 540 and rear slider 541. The rear slider 541 is formed of an upper part 546 in which the side surfaces insertable into an operating part body 545 form curved surfaces and a rectangular box-like lower part 547. The upper part 546 is provided on the front surface with a cylindrical guide tube inserting part 548 and on the outer periphery with three ribs 549. Two electrode inserting grooves 550 are provided from the lower side of the guide tube inserting part 548 to the upper part 546 and lower part 547. The lower part 547 is opened on the front surface and is provided on the sides with four engaging recesses 551 and inside the lower surface with ribs 554 forming an electrode receptacle 552 and an A-cord connecting part 553. The lower part 547 is provided on the rear surface with a thumb hanger 555.

The front slider 540 is a plate-like member consisting of a rectangular lower part 556 and an upper part 557 covering and shading the electrode inserting grooves 550 of the upper part 546 of the rear slider 541 in case the above mentioned lower part 556 and rear slider 541 are combined and is provided on the rear surface with a rib 559 having four pawls 558 engaging with the four recesses 551 of the rear slider 541. Further, the lower part 556 is provided on the lower side with an electrode presser 560 and U-like projection 561 to be fitted respectively in the electrode receptacle 552 and A-cord connecting part 553 of the rear slider 541.

The method of assembling the slider 543 and electrode 542 shall be explained in the following.

In the fifth embodiment, the shaft 422 of the electrode 421 is inserted through the electrode inserting hole 432 of the front slider 429, is bent and is fitted with the embedded member 433 and then the rear slider 441 is combined but, in this embodiment, first the electrode 542 is bent and is fitted with the embedded member 433 and then is fitted in the electrode inserting grooves 550 of the rear slider 541 and the front slider 540 may be fitted to the rear slider 541. The pawl part 558 of the front slider 540 is engaged with the recesses 551 of the rear slider 541 to fix both the same as in the fifth embodiment. Thus, as the electrode 542 can be bent without being passed through the front slider, an accurate bending position can be easily determined without being obstructed by the front slider 540 as in the fifth embodiment.

In this case, the electrode 542 is held at one rear end by the electrode receptacle 552 and electrode presser 560 and is fixed to the slider 543 and a metal part 562 at the rear end of the electrode 542 projects into the A-cord connecting part 553. The parts of the electrode fitted in the electrode inserting grooves 550 are pressed and fixed by the upper part 557 of the front slider 540.

In the case of a treatment, the slider connecting part 563 of the A-cord 544 is inserted into the A-cord connecting part 553 of the slider 543 and the electrode 542 and A-cord 544 are electrically connected with each other. In this embodiment, as the A-cord 544 comes out of the lower side of the slider 543, there is an effect that the A-cord will be less in the way during operation than in the eighth embodiment.

The other structures, operations and effects are the same as in the fifth embodiment. BY the way, this embodiment may be applied to the sixth and seventh embodiments.

FIGS. 52 to 55 show the tenth embodiment of the present invention.

This embodiment shows an electrode 606 to be fitted to the operating part 520 described in the seventh embodiment.

This electrode 606 comprises a shaft part 622a as a holding part inserted through a sheath 402, a forked part 622b on the tip side of this shaft part 622a and a loop 622c (tip electrode) formed to be arcuate by bending this forked part 622b at the tip downward so as to be substantially at right angles with the shaft part 622a.

The above mentioned forked part 622b is bent upward (in case the shaft part 622a is inserted as deviated downward through the sheath 602a) at a comparatively large angle with the axial direction of the shaft part 622a as shown in FIG. 53 in the parts (represented by the reference numeral 622b and mentioned as branch parts) from the shaft part 622a to the parallel rods branched and having a predetermined distance W, then the forked parallel parts 622e parallel with each other are projected upward and forward at a small angle with the shaft part 622a and a resecting part 622c is formed at the tips of the forked parallel parts 622e. This loop 622c is made of a wire 623 as such electrode conducting part as of a tungsten wire. The parts extended rearward from the loop 622c of this wire 623 are inserted through I-pipes 624a and 624b and are fixed to the I-pipes 624a and 624b by soldering or bonding. The I-pipes 624a and 624b are coated with insulating tubes 625a and 625b made of such electric insulating material as an ethylene tetrafluoride resin. The tip parts 626a and 626b of these insulating tubes 625a and 625b are molded to be of an outside diameter smaller than the outside diameter of the other parts of the insulating tubes 625a and 625b An insulating member 627 is internally fitted and secured by such means as bonding inside the insulating tube 625a at the rear end to secure watertightness Further, the insulating tubes 625a and 625b are coated respectively with O-pipes 628a and 628b secured by such means as soldering or bonding with each other at the rear ends The insulating tube 625a has such length that its rear end surface may be substantially in the same plane as of the rear end surface of the O-pipe 628a but the other insulating tube 625b projects rearward from the rear end of the O-pipe 628a, has the wire 623 and I-pipe 624b inserted through it and forms the shaft part 622a. Also, the wire 623 and I-pipe 624b project from the rear end of the insulating tube 625b to form a slider connecting part 629.

A guide pipe 630 to be cylindrical is fixed by such means as soldering or bonding in the axial direction on the upper sides of the O-pipes 628a and 628b in the parts secured to each other of the O-pipes 628a and 628b so as to prevent the rotary twist of the entire electrode 606 and to smoothly move the electrode 606 forward and rearward.

This guide pipe 630 is formed of such material as a metal or plastics so that the guide tube 521 may be inserted through the substantially cylindrical inside.

The great feature of this embodiment is that, as the tip parts 626a and 626b of the insulating tubes 625a and 625b are made small in the diameter and have an angle θ with the shaft part 622a, as shown in FIG. 55, the tip parts 626a and 626b will be able to come deep into the clearance between the optical sighting tube 404 and the inside diameter of the insertable part 607 of the sheath 402, the loop 622c will be able to be made larger and a larger tissue piece will be able to be resected in one operation. In case the insulating tubes 625a and 625b are small in the diameter over the entire length, the wall thicknesses of the insulating tubes 625a and 625b will reduce and therefore the insulation will reduce. On the contrary, in case they are formed to be large in the diameter over the entire length, the length of the loop 622c will become short and the resecting capacity will reduce. The other formations, operations and effects are the same as in the seventh embodiments.

Figure 56:
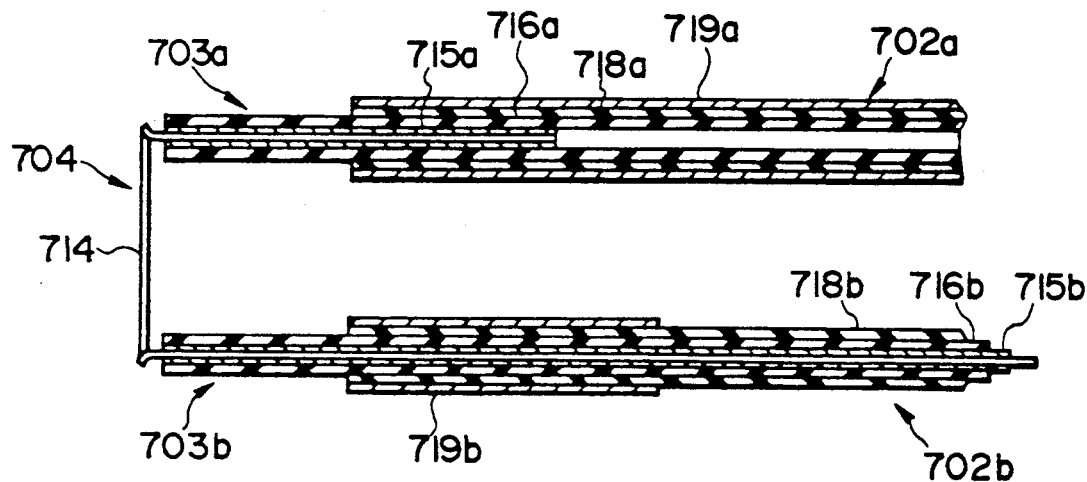
FIGS. 56 and 57 relate to the embodiment of the present invention.
Figure 57:
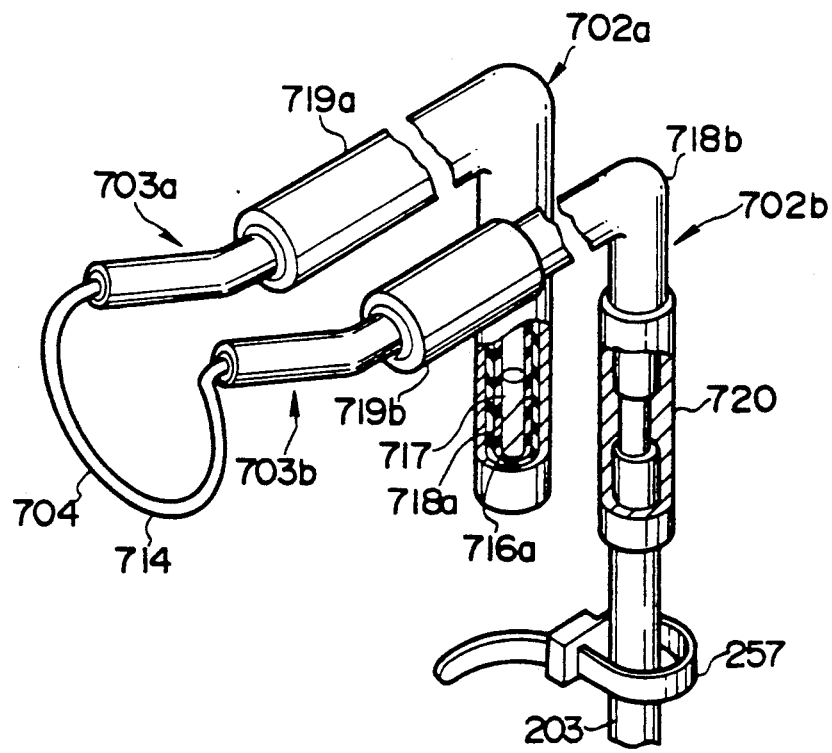

FIGS. 56 and 57 show the 11th embodiment of the present invention in which the electrode 642 is shown fitted to the operating part 201 described in the third embodiment as shown in FIGS. 10-17, elements of which embodiment are referred to below by their reference numerals.

The electrode part 642 comprises shaft parts 702a and 702b as holding parts inserted through guide pipes 243 secured on both lower sides of the tip of a guide tube 225, extended parallelly to a slider part 206 along the guide tube 225 and bent downward at right angles with the guide tube 225 within the slider part 206, a cord part 203 connected electrically and mechanically to the rear end of the shaft part 702b within the slider part 206 and extended to the outside of the slider part 206, parallel parts 703a and 703b provided on the tip sides of the shaft parts 102a and 102b and projected upward and forward at a small angle θ with the shaft parts 702a and 702b from the guide pipes 243 in case the electrode part 642 is retracted into the body 207 and a loop 704 connecting these parallel parts 703a and 703b at both tips, set substantially at right angles with the shaft parts 702a and 702b, bent downward and forming an arcuate loop.

The above mentioned loop 704 is made of a wire 714 as such electric conductive part as a tungsten wire and is extended to several cm. from the tip within the shaft part 702a and to the rear end of the shaft part 702b within the space 254 within the slider part 206 from the tip within the shaft part 702b.

The wire 714 is coated and fixed over the entire length except the loop 704t with I-pipes 715a and 715b made of stainless steel. Further, the I-pipes 715a and 715b are coated and fixed with inside insulating tubes 716a and 716b made of such electric insulating material as an ethylene tetrafluoride resin. The inside insulating tube 716a is further extended rearward from the rear end of the I-pipe 715a through the shaft part 702a to the groove 250 within the slider part 206. An insulating member 717 is fitted and secured by such means as bonding inside the rear end of the inside insulating tube 716a to secure the watertightness within the inside insulating tube 716a.

The shaft parts 702a and 702b provided at the rear ends of the parallel parts 703a and 703b are coated outside the inside insulating tubes 716a and 716b over the entire length with outside insulating tubes 718a and 718b formed of such insulating material as an ethylene tetrafluoride resin and are fixed with a bonding agent or the like. Further, the outside insulating tube 718a is coated outside over the entire length to the groove 250 within the slider part 250 with an O-pipe 719 made of stainless steel or the like and is fixed with a bonding agent or the like. The outside insulating tube 718b is coated outside with the O-pipe 719b only in the range in which it will be inserted through the guide pipes 243 in case the electrode part 642 is slid with respect to the body 207 and is fixed with a bonding agent or the like.

The wire 714b within the shaft part 702b led to the space 254 within the slider part 206 is electrically connected at the rear end with a core wire not illustrated of the cord part 203 as by soldering and the connecting part is contained within the space 254 as insulated and coated with a thermocontracting tube 256. A clamp 257 is wound and fixed to the connected cord part 203 at the lower end within the space 254 so that, even if the cord part 203 is pulled from outside, it will not be removed from the clamp 257.

The great feature of this embodiment is that, as the sliding parts of the shaft parts 702a and 702b of the electrode part 642 with the guide pipes 243 are made in double structures of the pipe members by using the I-pipes 715a and 715b and O-pipes 719a and 719b, the strength of these parts which will become fulcra in case a bending moment is applied to the loop 704 will be increased, the stiffness will be thereby increased and, even if a force is applied to the loop 704, the shaft parts 702a and 702b will not buckle and a stabilized resection will be able to be made.

As the wire 714a and I-pipe 715a are cut in the position several cm. inside the tip of the shaft part 702a, the area of the O-pipe 719a coating these high frequency current conducting parts through the inside insulating tube 716a and outside insulating tube 718a will reduce, the O-pipe 719b coating the wire 714b and I-pipe 715b will be only of the length of the sliding part with the guide pipe 243, the area of coating the high frequency current conducting part will be reduced and therefore the leaking current amount will be able to be greatly reduced.

Further, as the insulating tube is also of a double structure of the inside insulating tubes 716a and 716b and outside insulating tubes 718a and 718b and the parallel parts 703a and 703b projecting upward at a small angle from the shaft parts 710a and 710b are coated only with the inside insulating tubes 716a and 716b, the outside diameter of the parallel parts 703a and 703b will be able to be made smaller than of the shaft parts 702a and 702b. As the tip part is inserted deep in the clearance between the optical sighting tube 404 and the inside diameter of the insertable part of the sheath 402 as in FIG. 55, the length of the loop 704 will be able to be made large and a large tissue piece will be able to be resected in one operation. Further, as the insulating tube is of a double structure, a special tube made thin at the tip need not be prepared and a cheap tube will be able to be used.

The other formations, operations and effects are the same as in the third embodiment.

FIGS. 58 to 62 show the 12th embodiment of the present invention.

Figure 58:
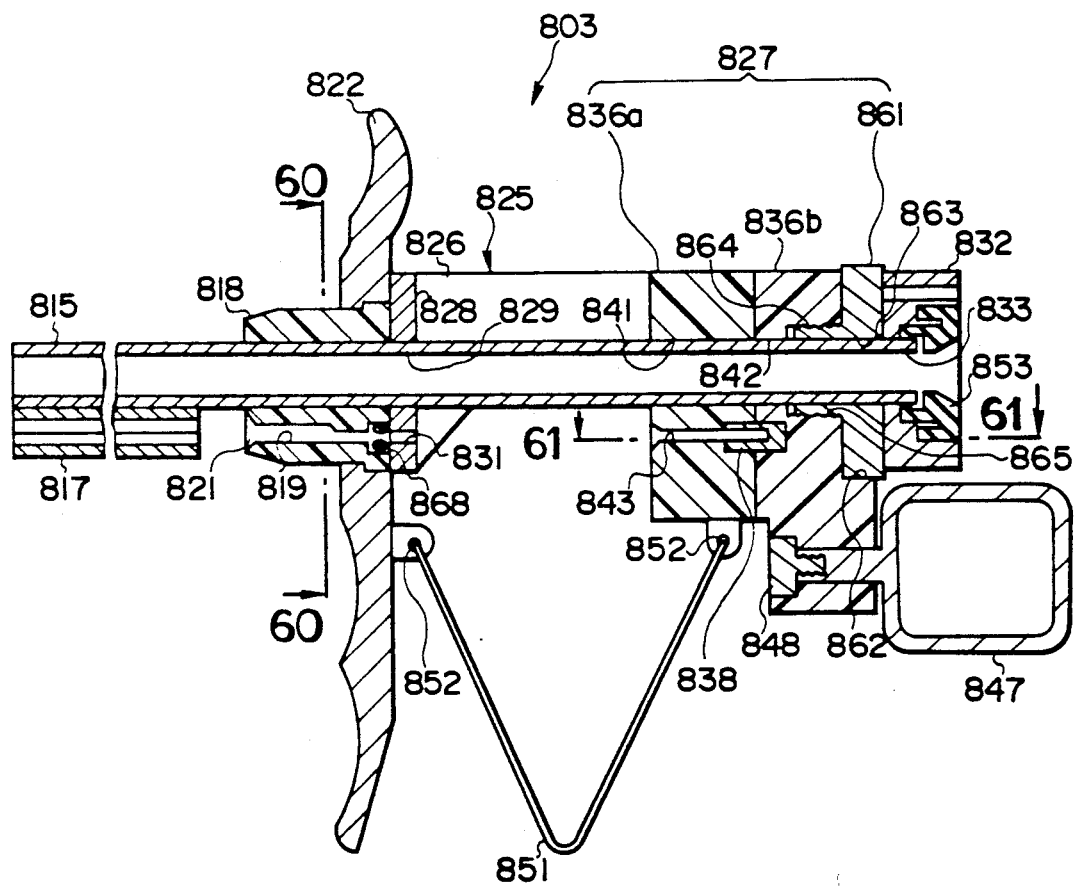

The operating part 803 in this embodiment is provided with a guide tube 815 inserted through the above mentioned sheath 2 of FIG. 1. An electrode inserting tube 817 through which the electrode 5 can be inserted is secured parallelly below the front part of this guide tube 815 as shown in FIG. 58. A sheath connecting part 818 formed of such insulating material as plastics is secured on the hand base side at a distance of about 10 mm. from the rear end of this electrode inserting tube 817 and is provided with an electrode inserting hole 819 so as to be aligned with this electrode inserting tube 817. By the way, a large chamfer 821 is formed in the front part of the electrode inserting hole 819 on this sheath connecting part 818.

Figure 60:
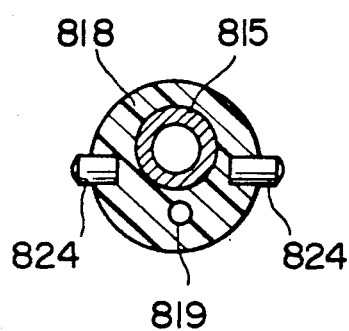

The above mentioned sheath connecting part 818 is fitted with a vertically projecting finger hanger 822 and is provided on the right and left as shown in FIG. 60 respectively with sheath connecting pins 824 to project. By the way, the finger hanger 822 and connecting pins 824 may be formed of such insulating material as plastics or of a metal.

The above mentioned operating part 803 has the operating part body 825 secured in the rear of the sheath connecting part 818. This operating part body 825 is made like a frame by providing a vertically opening space in the axial direction of the above mentioned guide tube 815. Within this space 826, a slider 827 is fitted movably in the axial direction.

As shown in FIG. 58, the above mentioned operating part body 825 is provided in the front part 828 with a guide tube inserting hole 829 through which the above mentioned guide tube 815 can be inserted and an electrode inserting hole 831 through which the above mentioned electrode 5 is passed in parallel with each other. The above mentioned guide tube 815 projects into a space 826 inside the operating part body 825 through this guide tube inserting hole 829 and is fitted at the rear end into a hole 833 provided in the rear part 832 of this operating part body 825. By the way, the sheath connecting part 818 fitted with the above mentioned guide tube 815 is not secured to the operating part body 825 but can be fixed by fitting the finger hanger 822 in FIG. 63 to the operating part body 825 with screws 834 as shown in FIG. 68. Therefore, by removing these screws 834, the finger hanger 822 can be separated from the operating part body 825 together with the sheath connecting part 818 and guide tube 815.

Figure 59:
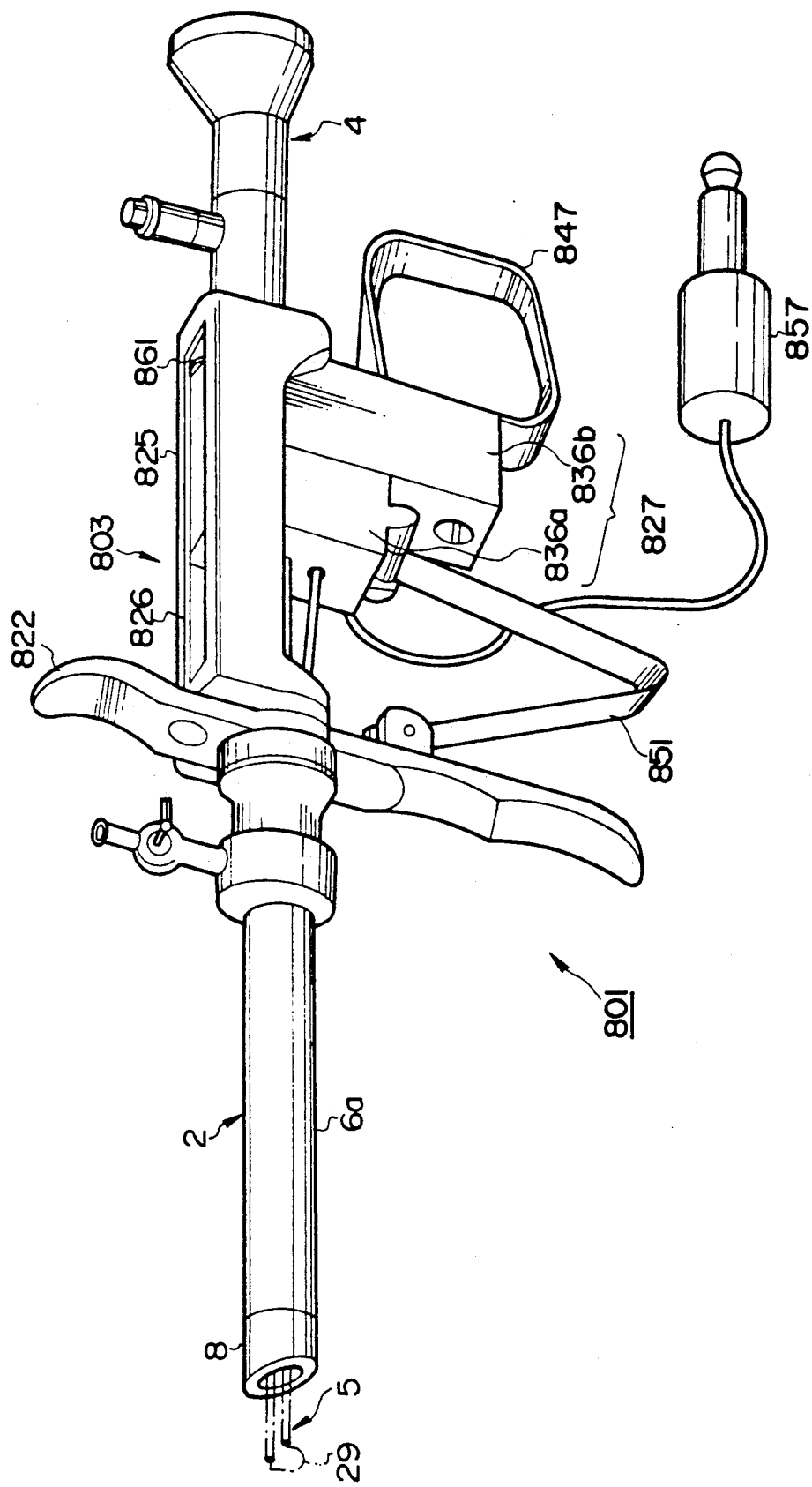

The slider 827 which can be contained in the upper side part within the space 826 of the above mentioned operating part body 825 comprises a slider front part 836a and slider rear part 836b as shown in FIG. 59 or 63, holding inside an electrode receptacle 838 from which an electrode cord 837 is extended and made integral by such means as bonding. The above mentioned slider front part 836a and slider rear part 836b are formed of such insulating material as plastics.

The above mentioned slider front part 836a and slider rear part 836b are provided respectively with guide tube inserting holes 841 and 842 having the same diameter as of or a diameter somewhat larger than the outside diameter of the guide tube 815 and able to pass the guide tube 815 so as to be slidable in the axial direction of this guide tube 815.

Figure 61:
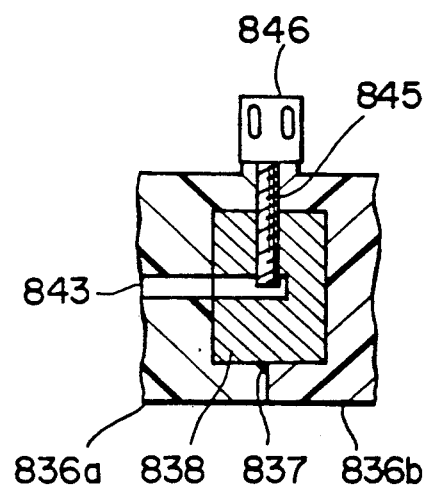

An electrode inserting hole 843 through which the electrode 805 can be passed is provided through the above mentioned slider front part 836a and electrode receptacle 838. As shown in FIG. 61 or 63, a set screw 845 free to project and retreat and reaching at the tip the electrode inserting hole 843 is screwed in from outside the side of the slider 827.

By the way, this set screw 845 is fitted at the rear end with a grip 846 made of an insulating material.

On the lower rear end surface of the above mentioned slider rear part 836b, a finger hanging ring 847 is rotatably fitted rearward by a screw 848.

By the way, a plug 857 connectable with a high frequency current source apparatus not illustrated is fitted to the rear end of the electrode cord 837 extended from the electrode receptacle 838.

A plate spring 851, for example, of a V-shape is rotatably fitted to the above mentioned finger hanger 822 and the lower end of the slider front part 836 respectively with pins 852 so that the slider 827 may be energized by the resiliency of the plate spring 851 to usually butt against the front surface of the rear part 832 of the operating part body 825. By the way, a rubber cap 853 securing the watertightness at the time of inserting the optical sighting tube 4 is fitted into the hole 833 of the above mentioned rear part 832.

Now, in this 12th embodiment, as shown, for example, in FIG. 58 or 63, on the rear end surface of the slider rear part 836b, a disc-like groove 862 for fitting and containing an adjusting ring 861 is provided coaxially with the above mentioned guide tube inserting hole 842 and a means whereby the position of the loop 29 at the tip of the electrode 5 can be adjusted for the sheath tip by the contained amount contained within the groove 862 (or the projected amount of the adjusting ring 861 projected from the rear surface of the slider rear part 836b) is formed.

The above mentioned ring 861 is in the form of a disc having a guide tube 815 inserting hole 863 in the center as shown in FIG. 58 or 63 and a projection is provided in the center of one surface (front surface) of the disc to form a male screw 864 which can be screwed into a threaded hole 865 of the slider rear Part 836b. This adjusting ring is set to be of such outside diameter that a part of the outer periphery of the ring will project out of an upper incision of the groove 862 in case this adjusting ring 861 is fitted in the groove 862 so that, by rotating this projecting part, the position of the slider 827 or electrode 5 may be adjusted in the axial direction.

For example, in FIG. 58, if the screw 864 of the adjusting ring 861 is further screwed in, this adjusting ring 861 will reduce in the amount of projecting out of the rear end surface of the slider rear part 836b. As the rear end surface of this adjusting ring 861 is energized by the resiliency of the plate spring 851 to contact the front surface of the rear part 832 of the operating part body 803, the larger the amount of screwing in the above mentioned adjusting ring 861, the more the electrode 805 fitted to the slider 827 will move rearward. Therefore, the position of the tip of the electrode 5 in FIG. 62 can be variably adjusted in the axial direction by this adjusting ring 861.

By the way, the above mentioned slider 827 can be separated from the operating part body 825 together with the finger hanger 822, sheath connecting part 818 and guide tube 815 by removing the above mentioned screws 834.

An O-ring 868 securing the watertightness in case the electrode 5 is inserted by expanding the diameter is fitted in the rear part 867 of the electrode inserting hole 819 of the sheath connecting part 818.

Figure 62:
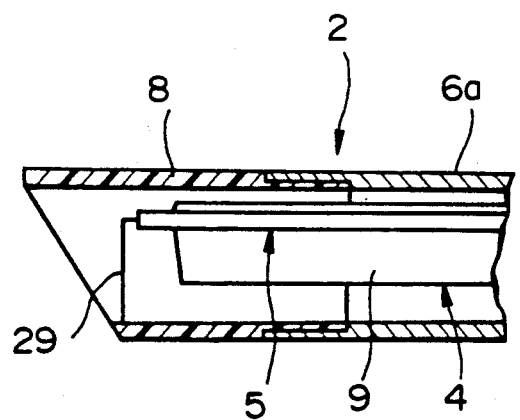

In the case of making resection, in order to positively hold the affected part together with the tip of the sheath 802, the loop 29 must be completely pulled into the sheath 2. However, as shown in FIG. 62, near the tip of the sheath 2, the tip of the insertable part 9 of the optical sighting tube 4 formed of a metal pipe is so arranged that the affected part may be observed from the tip opening of the sheath 2. However, in order to prevent the visual field from being obstructed by the tip of the sheath 2, the insertable part can not be arranged in a position of pulling it in too deep from the tip of the sheath 2. Therefore, if the loop 29 is pulled into the sheath 2 too much, then the insertable part 9 tip and the loop 29 will come so near to each other that a spark will pass from the loop 29 to the insertable part 9, an electric current will flow to the operator through the optical sighing tube 4 and there will be a danger of causing a burn.

However, in this 12th embodiment, as the adjusting ring 861 is provided in the rear part of the slider 827 and, by rotating this adjusting ring 861, the position of the electrode 5 can be adjusted together with the slider 827 for the sheath 2 and the optical sighting tube 4 fitted to the operating part 803 fitted to the sheath 2, the loop 29 at the tip of the electrode 5 will be able to be set in the optimum position between the tip of the sheath 2 and the tip of the optical sighting tube 4 at any time by using such tool as a screw driver. Therefore, the generation of the spark in the above description can be prevented and the safety can be elevated.

Even if the dimensional tolerances of such lengths of the respective parts for determining the position relations as the length of the insertable part 9 of the optical sighting tube 4 and the total length of the electrode 5 are alleviated, the position will be able to be adjusted after the assembly. Therefore, there are advantages that the part precision and assembly precision can be alleviated and the production cost can be reduced.

By the way, in this embodiment, as the guide tube is formed as one over the entire length of the insertable part of the optical sighting tube 4, there is a further advantage that the strength can be improved to be higher than in the second embodiment.

The other formations, operations and effects are the same as in the second embodiment.

As explained above, according to the present invention, as at least one of the electrode and cord and the operating part are made integral, the number of the electric contacts between the electrode and cord likely to cause current leaks and contact failures in the operating part will be able to be reduced and the electric safety and stability will be able to be improved.

What is claimed is:

1. A resectoscope apparatus comprising:
   an elongate hollow sheath to be inserted into a body cavity;
   an endoscope having an insertable part including an optical system inserted through said sheath for making the body cavity observable;
   an operating part connected to said sheath;
   a slider provided in said operating part, said slider including an electrode and a cord connected to said electrode for feeding a high frequency current from a high frequency current source to said electrode, said electrode being inserted through said sheath for making such treatment as resecting or coagulating tissues within a body cavity by using high frequency current;
   said electrode being mounted in said slider and projecting therefrom in a sliding direction, said slider being movable with respect to said operating part in said sliding direction for inserting said electrode through said sheath, and
   said electrode having a bent portion within said slider bending away from said sliding direction, said electrode being fixed to said slider by a holding part within said slider formed to hold said electrode at least one of said bent portion and a terminal portion proximal to said bent portion.

2. A resectoscope apparatus according to claim 1 wherein said bent portion of said electrode is bent at substantially a right angle away from said sliding direction.

3. A resectoscope apparatus according to claim 1 wherein said terminal portion is shaped like a shaft and said slider holding part is formed with a groove to accept said shaft-like portion.

4. A resectoscope apparatus according to claim 1 wherein said cord is connected to said terminal portion of said electrode within said slider.

5. A resectoscope apparatus according to claim 1 wherein said terminal portion of said electrode is projected from said slider, and said cord is removably connected to said terminal portion.

6. A resectoscope apparatus according to claim 1 wherein said operating part includes a guide tube in which said insertable part is inserted, said guide tube is removably connected to said operating part by a body connecting part which is externally fitted to said guide tube and includes an electrode inserting hole in which said guide tube is inserted, and said electrode is inserted into said electrode inserting hole provided in said body connecting part.

7. A resectoscope apparatus according to claim 1 wherein said body connecting part has a sheath connecting part for removably connecting said sheath and said operating part.

8. A resectoscope apparatus according to claim 1 wherein said electrode comprises two shafts projecting in said sliding direction and at least one of said shafts has a terminal bent portion fixed by said holding part within said slider.

9. A resectoscope apparatus according to claim 1 further comprising a position regulating means capable of adjusting a position of a tip of said electrode with respect to said sheath and said endoscope insertable part.

10. A resectoscope apparatus according to claim 9 wherein said position regulating means is provided in said slider.

11. A resectoscope apparatus according to claim 9 wherein said position regulating means includes a fixing mechanism to fix a position of said electrode.

12. A resectoscope apparatus according to claim 9 wherein said position regulating means is provided in a rear part of said operating part.

13. A resectoscope apparatus according to claim 1 wherein said electrode has a treating part including a tip for treating tissues within a body cavity and an arm arranged at a fixed distance in a diametral direction of said endoscope insertable part for holding said treating part, said arm being provided with an electric conductive part and an electric insulating member coating said electric conductive part, and said electric insulating member being formed to have an outside diameter on an operating part side that is larger than an outside diameter at the treating tip.

14. A resectoscope apparatus according to claim 3 wherein said arm is branched at a tip into two shaft parts which are connected to said treating part.

15. A resectoscope apparatus according to claim 3 wherein said arm is formed of two shaft parts which are fixedly incorporated at rear ends in said slider, and said cord is fixedly connected to one shaft part at a rear end thereof.

16. A resectoscope apparatus comprising:
an elongate hollow sheath to be inserted into a body cavity;
an endoscope having an insertable part including an optical system inserted through said sheath for making the body cavity observable;
an operating part connected to said sheath;
a slider provided in said operating part, said slider including an electrode and a cord connected to said electrode for feeding a high frequency current from a high frequency current source to said electrode, said electrode being inserted through said sheath for making such treatment as resecting or coagulating tissues within a body cavity by using high frequency current;
said electrode being mounted in said slider and projecting therefrom in a sliding direction, said slider being movable with respect to said operating part in said sliding direction for inserting said electrode through said sheath, wherein said slider is formed of at least two parts fitting together, and said electrode is fixed to the slider by sandwiching the electrode between two said parts.

17. A resectoscope apparatus according to claim 16 wherein said slider is divided along a surface perpendicular to said sliding direction to fit around said electrode.

18. A resectoscope apparatus according to claim 16 wherein said slider parts are formed to fix together by a snap fit when fitted together.

19. A resectoscope apparatus according to claim 16 wherein, when said two said parts are fitted together, a groove in which the electrode can be housed is provided in at least one of said two said parts.

20. A resectoscope apparatus according to claim 19 wherein said terminal portion of said electrode projects from said slider and is sandwiched between said two said parts and said cord is removably connected to said terminal portion.

21. A resectoscope apparatus according to claim 16 further comprising a position regulating means capable of adjusting a position of a tip of said electrode with respect to said sheath and said endoscope insertable part.

22. A resectoscope apparatus according to claim 21 wherein said position regulating means is provided in said slider.

23. A resectoscope apparatus according to claim 21 wherein said position regulating means includes a fixing mechanism to fix a position of said electrode.

24. A resectoscope apparatus according to claim 21 wherein said position regulating means is provided in a rear part of said operating part.

25. A resectoscope apparatus according to claim 16 wherein said electrode has a treating part including a tip for treating tissues within a body cavity and an arm arranged at a fixed distance in a diametral direction of said endoscope insertable part for holding said treatment part, said arm being provided with an electric conductive part and an electric insulating member coating said electric conductive part, and said electric insulating member being formed to have an outside diameter on an operating part side that is larger than an outside diameter at the treating tip.

26. A resectoscope apparatus according to claim 25 wherein said arm is branched at a tip into two shaft parts which are connected to said treating part.

27. A resectoscope apparatus according to claim 25 wherein said arm is formed of two shaft parts which are fixedly incorporated at rear ends in said slider, and said cord is fixedly connected to one shaft part at a rear end thereof.

28. A resectoscope apparatus comprising:
an elongate hollow sheath to be inserted into a body cavity;
an endoscope having an insertable part including an optical system inserted through said sheath for making the body cavity observable;
an operating part connected to said sheath;
a slider provided in said operating part, said slider including an electrode and a cord connected to said electrode for feeding a high frequency current from a high frequency current source to said electrode, said electrode being inserted through said sheath for making such treatment as resecting or coagulating tissues within a body cavity by using high frequency current;
said electrode being mounted in said slider and projecting therefrom in a sliding direction, said slider being movable with respect to said operating part in said sliding direction for inserting said electrode through said sheath, wherein said electrode and cord are insulated at connecting parts thereof so as to prevent contact with fluids at the connection, said electrode being fixed to said slider at said holding part and said electrode and cord connecting parts being housed within said slider.

29. A resectoscope apparatus according to claim 28, wherein said slider is formed with a groove therewithin for receiving said electrode and cord connecting parts.

30. A resectoscope apparatus according to claim 28, wherein said electrode and cord connecting parts are insulated by covering with a thermal shrinking tube.

31. A resectoscope apparatus according to claim 28, wherein said operating part includes a guide tube in which said insertable part is inserted, said guide tube is removably connected to said operating part by a body connecting part which is externally fitted to said guide tube and includes an electrode inserting hole in which said guide tube is inserted, and said electrode is inserted into said electrode inserting hole provided in said body connecting part.

32. A resectoscope apparatus according to claim 28, wherein said body connecting part has a sheath connecting part for removably connecting said sheath and said operating part.

33. A resectoscope apparatus according to claim 28, wherein said electrode comprises two shafts, an end of one said shaft being connected to said cord and an end of the other said shaft being insulatedly housed within said slider.

34. A resectoscope apparatus according to claim 28, further comprising a position regulating means capable of adjusting a position of a tip of said electrode with respect to said sheath and said endoscope insertable part.

35. A resectoscope apparatus according to claim 34 wherein said position regulating means is provided in said slider.

36. A resectoscope apparatus according to claim 34 wherein said position regulating means includes a fixing mechanism to fix a position of said electrode.

37. A resectoscope apparatus according to claim 34 wherein said position regulating means is provided in a rear part of said operating part.

38. A resectoscope apparatus according to claim 28 wherein said electrode has a treating part including a tip for treating tissues within a body cavity and an arm arranged at a fixed distance in a diametral direction of said endoscope insertable part for holding said treating part, said arm being provided with an electric conductive part and an electric insulating member coating said electric conductive part, and said electric insulating member being formed to have an outside diameter on an operating part side that is larger than an outside diameter at the treating tip.

39. A resectoscope apparatus according to claim 38 wherein said arm is branched at a tip into two shaft parts which are connected to said treating part.

40. A resectoscope apparatus according to claim 38 wherein said arm is formed of two shaft parts which are fixedly incorporated at rear ends in said slider, and said cord is fixedly connected to one shaft part at a rear end thereof.

41. A resectoscope apparatus comprising:
an elongate hollow sheath to be inserted into a body cavity;
an endoscope having an insertable part including an optical system inserted through said sheath for making the body cavity observable;
an operating part connected to said sheath;
a slider provided in said operating part, said slider including an electrode and a cord connected to said electrode for feeding a high frequency current from a high frequency current source to said electrode, said electrode being inserted through said sheath for making such treatment as resecting or coagulating tissues within a body cavity by using high frequency current;
said electrode being mounted in said slider and projecting therefrom in a sliding direction, said slider being movable with respect to said operating part in said sliding direction for inserting said electrode through said sheath, and
said electrode having a bent portion within said slider bending away from said sliding direction, said electrode being fixed to said slider by a holding part within said slider formed to hold said electrode at least one of said bent portion and a terminal portion proximal to said bent portion;
wherein said slider is formed of at least two parts fitting together, and said electrode is fixed to the slider by sandwiching the electrode between two said parts.

42. A resectoscope apparatus comprising:
an elongate hollow sheath to be inserted into a body cavity;
an endoscope having an insertable part including an optical system inserted through said sheath for making the body cavity observable;
an operating part connected to said sheath;
a slider provided in said operating part, said slider including an electrode and a cord connected to said electrode for feeding a high frequency current from a high frequency current source to said electrode, said electrode being inserted through said sheath for making such treatment as resecting or coagulating tissues within a body cavity by using high frequency current;
said electrode being mounted in said slider and projecting therefrom in a sliding direction, said slider being movable with respect to said operating part in said sliding direction for inserting said electrode through said sheath, and
said electrode having a bent portion within said slider bending away from said sliding direction, said electrode being fixed to said slider by a holding part within said slider formed to hold said electrode at least one of said bent portion and a terminal portion proximal to said bent portion;
wherein said electrode and cord are insulated at connecting parts thereof so as to prevent contact with fluids at the connection, said electrode being fixed to said slider at said holding part and said electrode and cord connecting parts being housed within said slider.

43. A resectoscope apparatus comprising:
an elongate hollow sheath to be inserted into a body cavity;
an endoscope having an insertable part including an optical system inserted through said sheath for making the body cavity observable;
an operating part connected to said sheath;
a slider provided in said operating part, said slider including an electrode and a cord connected to said electrode for feeding a high frequency current from a high frequency current source to said electrode, said electrode being inserted through said sheath for making such treatment as resecting or coagulating tissues within a body cavity by using high frequency current;
said electrode being mounted in said slider and projecting therefrom in a sliding direction, said slider being movable with respect to said operating part in said sliding direction for inserting said electrode through said sheath, and
wherein said slider is formed of at least two parts fitting together, and said electrode is fixed to the slider by sandwiching the electrode between two said parts; and
wherein said electrode and cord are insulated at connected parts thereof so as to prevent contact with fluids at the connection, said electrode being fixed to said slider at said holding part and said electrode and cord connecting parts being housed within said slider.

44. A resectoscope apparatus comprising:
an elongate hollow sheath to be inserted into a body cavity;
an endoscope having an insertable part including an optical system inserted through said sheath for making the body cavity observable;
an operating part connected to said sheath;
a slider provided in said operating part, said slider including an electrode and a cord connected to said electrode for feeding a high frequency current from a high frequency current source to said electrode, said electrode being inserted through said sheath for making such treatment as resecting or coagulating tissues within a body cavity by using high frequency current;
said electrode being mounted in said slider and projecting therefrom in a sliding direction, said slider being movable with respect to said operating part in said sliding direction for inserting said electrode through said sheath, and said electrode having a bent portion within said slider bending away from said sliding direction, said electrode being fixed to said slider by a holding part within said slider formed to hold said electrode at least one of said bent portion and a terminal portion proximal to said bent portion;

wherein said slider is formed of at least two parts fitting together, and said electrode is fixed to the slider by sandwiching the electrode between two said parts; and wherein said electrode and cord are insulated at connecting parts thereof so as to prevent contact with fluids at the connection, said electrode being fixed to said slider at said holding part and said electrode and cord connecting parts being housed within said slider.

* * * * *